United States Patent
Leadley et al.

(10) Patent No.: US 11,452,826 B2
(45) Date of Patent: Sep. 27, 2022

(54) MECHANICAL CONNECTOR FOR ELECTRONIC VAPOR PROVISION SYSTEM

(71) Applicant: NICOVENTURES HOLDINGS LIMITTED, London (GB)

(72) Inventors: David Leadley, London (GB); Matthew Joel Nettenstrom, London (GB); Siddhartha Jain, London (GB)

(73) Assignee: Nicoventures Trading Limited, London (GB)

( * ) Notice: Subject to any disclaimer, the term of this patent is extended or adjusted under 35 U.S.C. 154(b) by 318 days.

(21) Appl. No.: 16/087,003

(22) PCT Filed: Mar. 21, 2017

(86) PCT No.: PCT/GB2017/050784
§ 371 (c)(1),
(2) Date: Sep. 20, 2018

(87) PCT Pub. No.: WO2017/163047
PCT Pub. Date: Sep. 28, 2017

(65) Prior Publication Data
US 2019/0098931 A1    Apr. 4, 2019

(30) Foreign Application Priority Data

Mar. 24, 2016  (GB) ...................................... 1605102
Aug. 2, 2016   (GB) ...................................... 1613322

(51) Int. Cl.
*A24F 13/00*     (2006.01)
*A61M 15/06*     (2006.01)
(Continued)

(52) U.S. Cl.
CPC ............. *A61M 15/06* (2013.01); *A24F 40/40* (2020.01); *A61M 11/042* (2014.02); *A24F 40/10* (2020.01);
(Continued)

(58) Field of Classification Search
CPC ...................................................... A24F 47/00
(Continued)

(56) References Cited

U.S. PATENT DOCUMENTS 3,048,307 A    8/1962  Daniel et al.
3,455,580 A    7/1969  Howard et al.
(Continued)

FOREIGN PATENT DOCUMENTS

AT    508244 A4    12/2010
CA    2505366 A1   10/2006
(Continued)

OTHER PUBLICATIONS

Decision for Korean Application No. 3020160038357_M002 dated Dec. 14, 2016., 3 pages.
(Continued)

*Primary Examiner* — Phuong K Dinh
(74) *Attorney, Agent, or Firm* — Patterson Thuente Pedersen, P.A.

(57) ABSTRACT

An electronic vapor provision system includes a cartridge for storing material heatable to generate an aerosol and a control unit housing a battery to provide electrical power for heating, the cartridge and the control unit separably connectable by at least one latching element, the latching element including a foot, and a leg joined at a first end to the foot by a flexible resilient joint and having a first latch member, the foot anchored within one of the cartridge and the control unit, and the other of the cartridge and the control unit having a second latch member on a surface, and positioned and configured to engage with the first latch member when the cartridge and the control unit are brought together with a substantially linear motion, and disengage with the first latch member when the cartridge and the control unit are pulled apart, the engagement and disengage-
(Continued)

ment enabled by movement of the leg of the latching element about the flexible resilient joint.

23 Claims, 6 Drawing Sheets

(51) Int. Cl.
  *A61M 11/04* (2006.01)
  *A24F 40/40* (2020.01)
  *A24F 40/10* (2020.01)

(52) U.S. Cl.
  CPC .............. A61M 2205/3653 (2013.01); A61M 2205/8206 (2013.01)

(58) Field of Classification Search
  USPC .................................................. 131/328–329
  See application file for complete search history.

(56) References Cited

U.S. PATENT DOCUMENTS

| | | |
|---|---|---|
| D250,485 S | 12/1978 | Cuthbertson |
| 4,235,498 A | 11/1980 | Snyder |
| 5,322,075 A | 6/1994 | Deevi et al. |
| 5,372,148 A | 12/1994 | McCafferty et al. |
| D367,526 S | 2/1996 | Bignon |
| 5,564,442 A | 10/1996 | MacDonald et al. |
| 5,840,279 A | 11/1998 | Narodylo et al. |
| D430,358 S | 8/2000 | Papiernik |
| D447,276 S | 8/2001 | Gustafson |
| 6,406,315 B1 | 6/2002 | Bates, III et al. |
| 6,418,926 B1 | 7/2002 | Chawla |
| D466,644 S | 12/2002 | Cohen Harel |
| D469,962 S | 2/2003 | Campbell et al. |
| 6,854,470 B1 | 2/2005 | Pu |
| D503,996 S | 4/2005 | Mabbutt |
| D504,947 S | 5/2005 | McAuley et al. |
| D505,514 S | 5/2005 | Liu |
| D514,222 S | 1/2006 | Anderson et al. |
| D518,171 S | 3/2006 | Anderson et al. |
| D560,793 S | 1/2008 | Pearl et al. |
| D569,967 S | 5/2008 | Pearl et al. |
| D572,406 S | 7/2008 | Masoud |
| D577,815 S | 9/2008 | Gokhale et al. |
| D579,544 S | 10/2008 | Birath et al. |
| D579,545 S | 10/2008 | Birath et al. |
| D579,546 S | 10/2008 | Birath et al. |
| D579,547 S | 10/2008 | Birath et al. |
| D579,548 S | 10/2008 | Birath et al. |
| D579,549 S | 10/2008 | Birath et al. |
| D579,550 S | 10/2008 | Birath et al. |
| D581,520 S | 11/2008 | Williams et al. |
| D583,463 S | 12/2008 | Wood et al. |
| D590,495 S | 4/2009 | Lulla et al. |
| D590,938 S | 4/2009 | Lulla et al. |
| D591,856 S | 5/2009 | Lulla et al. |
| D613,848 S | 4/2010 | Harvey et al. |
| D614,285 S | 4/2010 | Birath et al. |
| D629,886 S | 12/2010 | Adamo et al. |
| D637,280 S | 5/2011 | Harvey et al. |
| D637,281 S | 5/2011 | Harvey et al. |
| D637,282 S | 5/2011 | Harvey et al. |
| D639,414 S | 6/2011 | Berndt |
| D641,076 S | 7/2011 | Grunstad et al. |
| D646,780 S | 10/2011 | Lulla et al. |
| D659,236 S | 5/2012 | Bobjer et al. |
| D670,374 S | 11/2012 | Bobjer et al. |
| D671,207 S | 11/2012 | Bobjer et al. |
| D684,254 S | 6/2013 | Zuyderhoudt |
| D684,684 S | 6/2013 | Grunstad et al. |
| D692,997 S | 11/2013 | Lovell et al. |
| D693,963 S | 11/2013 | Akopyan |
| D700,227 S | 2/2014 | Kile |
| D700,738 S | 3/2014 | Rennick et al. |
| D710,002 S | 7/2014 | Valentine et al. |
| D711,528 S | 8/2014 | Grunstad et al. |
| D717,425 S | 11/2014 | Von Schuckmann |
| D726,364 S | 4/2015 | Weigensberg |
| D726,955 S | 4/2015 | Martin |
| 9,010,335 B1 | 4/2015 | Scatterday |
| D737,419 S | 8/2015 | Emarlou |
| D737,426 S | 8/2015 | Nakamura |
| D745,139 S | 12/2015 | Chen et al. |
| D745,660 S | 12/2015 | Gruntad et al. |
| D761,488 S | 7/2016 | Alarcon et al. |
| D769,438 S | 10/2016 | Crosby et al. |
| D770,088 S | 10/2016 | Abadi et al. |
| 9,504,279 B2 | 11/2016 | Chen |
| D782,109 S | 3/2017 | King |
| D790,123 S | 6/2017 | Beer et al. |
| D790,125 S | 6/2017 | Beer et al. |
| D790,767 S | 6/2017 | Rush et al. |
| D799,750 S | 10/2017 | Parcevaux |
| D820,514 S | 6/2018 | Durand |
| D820,515 S | 6/2018 | Nettenstrom et al. |
| D822,193 S | 7/2018 | Nitta |
| 2002/0040713 A1 | 4/2002 | Eisele et al. |
| 2003/0178024 A1 | 9/2003 | Allan et al. |
| 2003/0235538 A1 | 12/2003 | Zierenberg |
| 2004/0025865 A1 | 2/2004 | Nichols et al. |
| 2004/0025877 A1 | 2/2004 | Crowder et al. |
| 2004/0149283 A1 | 8/2004 | Hochrainer |
| 2005/0005934 A1 | 1/2005 | Harvey |
| 2005/0006273 A1 | 1/2005 | Chawla |
| 2005/0017017 A1 | 1/2005 | Crosby et al. |
| 2005/0022812 A1 | 2/2005 | Hrkach |
| 2005/0081846 A1 | 4/2005 | Barney |
| 2005/0103336 A1 | 5/2005 | Nishibayashi et al. |
| 2005/0103337 A1 | 5/2005 | Hickey et al. |
| 2005/0115562 A1 | 6/2005 | Chawla |
| 2005/0205685 A1 | 9/2005 | Jones |
| 2005/0247305 A1 | 11/2005 | Zierenberg et al. |
| 2005/0252511 A1 | 11/2005 | Pentafragas |
| 2005/0279357 A1 | 12/2005 | Wachtel |
| 2006/0102175 A1 | 5/2006 | Nelson |
| 2006/0157053 A1 | 7/2006 | Barney et al. |
| 2006/0157054 A1 | 7/2006 | Kuehn et al. |
| 2006/0163269 A1 | 7/2006 | Anderson et al. |
| 2006/0196518 A1 | 9/2006 | Hon |
| 2006/0237010 A1 | 10/2006 | De Boer et al. |
| 2006/0237016 A1 | 10/2006 | Wachtel |
| 2007/0045288 A1 | 3/2007 | Nelson |
| 2007/0052544 A1 | 3/2007 | Lintell |
| 2007/0114305 A1 | 5/2007 | Yamaguchi et al. |
| 2007/0125765 A1 | 6/2007 | Nelson |
| 2007/0131805 A1 | 6/2007 | Yamaguchi et al. |
| 2007/0137645 A1 | 6/2007 | Eason et al. |
| 2007/0152086 A1 | 7/2007 | Yamaguchi et al. |
| 2007/0181123 A1 | 8/2007 | Houzego |
| 2007/0186923 A1 | 8/2007 | Poutiatine et al. |
| 2007/0215149 A1 | 9/2007 | King et al. |
| 2007/0267031 A1 | 11/2007 | Hon |
| 2008/0099015 A1 | 5/2008 | Pocock et al. |
| 2008/0116220 A1 | 5/2008 | Pocock et al. |
| 2008/0196718 A1 | 8/2008 | Connell et al. |
| 2008/0295832 A1 | 12/2008 | Geser et al. |
| 2008/0295834 A1 | 12/2008 | Thoemmes et al. |
| 2008/0314384 A1 | 12/2008 | Harris et al. |
| 2009/0047821 A1* | 2/2009 | Chen .................. H01R 13/6275 439/358 |
| 2009/0084379 A1 | 4/2009 | Goeckner et al. |
| 2009/0133691 A1 | 5/2009 | Yamada et al. |
| 2009/0165791 A1 | 7/2009 | Wendland |
| 2009/0194105 A1 | 8/2009 | Besseler et al. |
| 2009/0205656 A1 | 8/2009 | Nishibayashi et al. |
| 2009/0250056 A1 | 10/2009 | Pentafragas |
| 2009/0277446 A1 | 11/2009 | Walz |
| 2009/0283095 A1 | 11/2009 | Pocock et al. |
| 2009/0293888 A1 | 12/2009 | Williams et al. |
| 2009/0293892 A1 | 12/2009 | Williams et al. |
| 2009/0314291 A1 | 12/2009 | Anderson et al. |
| 2010/0024812 A1 | 2/2010 | Sugita et al. |
| 2010/0024814 A1 | 2/2010 | Sugita et al. |

(56) References Cited

U.S. PATENT DOCUMENTS

| | | |
|---|---|---|
| 2010/0059050 A1 | 3/2010 | Wachtel |
| 2010/0059052 A1 | 3/2010 | Davies et al. |
| 2010/0083962 A1 | 4/2010 | Von Schuckmann |
| 2010/0154795 A1 | 6/2010 | Pentafragas |
| 2010/0163042 A1 | 7/2010 | Bhowmick et al. |
| 2010/0189780 A1 | 7/2010 | Walz et al. |
| 2010/0192949 A1 | 8/2010 | Wright et al. |
| 2010/0242960 A1 | 9/2010 | Zangerle |
| 2010/0258120 A1 | 10/2010 | Colomb |
| 2010/0294278 A1 | 11/2010 | Mosier et al. |
| 2011/0011396 A1 | 1/2011 | Fang |
| 2011/0041841 A1 | 2/2011 | Wachtel et al. |
| 2011/0067696 A1 | 3/2011 | Sato et al. |
| 2011/0094523 A1 | 4/2011 | Thorens et al. |
| 2011/0120463 A1 | 5/2011 | Esteve et al. |
| 2011/0120465 A1 | 5/2011 | Haerder et al. |
| 2011/0162642 A1 | 7/2011 | Akouka et al. |
| 2011/0174305 A1 | 7/2011 | Bunch et al. |
| 2011/0203586 A1 | 8/2011 | Egen et al. |
| 2011/0226236 A1 | 9/2011 | Buchberger |
| 2011/0226266 A1 | 9/2011 | Tao |
| 2011/0232637 A1 | 9/2011 | Kaemper et al. |
| 2011/0271958 A1 | 11/2011 | Sawant |
| 2011/0277757 A1 | 11/2011 | Terry et al. |
| 2011/0277760 A1 | 11/2011 | Terry et al. |
| 2011/0290249 A1 | 12/2011 | Schennum |
| 2012/0037157 A1 | 2/2012 | Rohrschneider et al. |
| 2012/0037158 A1 | 2/2012 | Wachtel et al. |
| 2012/0132205 A1 | 5/2012 | Meliniotis et al. |
| 2012/0199663 A1 | 8/2012 | Qiu |
| 2012/0247463 A1 | 10/2012 | Zoltan |
| 2012/0260917 A1 | 10/2012 | Bilgic |
| 2012/0318283 A1 | 12/2012 | Watanabe et al. |
| 2012/0325227 A1 | 12/2012 | Robinson et al. |
| 2013/0019887 A1 | 1/2013 | Liu |
| 2013/0025609 A1 | 1/2013 | Liu |
| 2013/0042865 A1 | 2/2013 | Monsees et al. |
| 2013/0047985 A1 | 2/2013 | Harris et al. |
| 2013/0081642 A1 | 4/2013 | Safari |
| 2013/0139815 A1 | 6/2013 | Colomb et al. |
| 2013/0152927 A1 | 6/2013 | Baillet et al. |
| 2013/0152928 A1 | 6/2013 | Kirniak |
| 2013/0160764 A1 | 6/2013 | Liu |
| 2013/0160765 A1 | 6/2013 | Liu |
| 2013/0174842 A1 | 7/2013 | Young et al. |
| 2013/0186398 A1 | 7/2013 | Baillet et al. |
| 2013/0192615 A1 | 8/2013 | Tucker et al. |
| 2013/0192616 A1 | 8/2013 | Tucker et al. |
| 2013/0206136 A1 | 8/2013 | Herrmann et al. |
| 2013/0228191 A1 | 9/2013 | Newton |
| 2013/0233313 A1 | 9/2013 | Young et al. |
| 2013/0255675 A1 | 10/2013 | Liu |
| 2013/0255679 A1 | 10/2013 | Andrade et al. |
| 2013/0269687 A1 | 10/2013 | Besseler et al. |
| 2013/0269695 A1 | 10/2013 | Brouet et al. |
| 2013/0306065 A1 | 11/2013 | Thorens et al. |
| 2013/0319440 A1 | 12/2013 | Capuano |
| 2013/0327327 A1 | 12/2013 | Edwards et al. |
| 2013/0340778 A1 | 12/2013 | Liu |
| 2014/0000601 A1 | 1/2014 | Arvidsson et al. |
| 2014/0007875 A1 | 1/2014 | Berg et al. |
| 2014/0053858 A1 | 2/2014 | Liu |
| 2014/0069420 A1 | 3/2014 | Richter et al. |
| 2014/0076310 A1 | 3/2014 | Newton |
| 2014/0076315 A1 | 3/2014 | Von Schuckmann |
| 2014/0083422 A1 | 3/2014 | Arvidsson et al. |
| 2014/0109921 A1 | 4/2014 | Chen |
| 2014/0123989 A1 | 5/2014 | LaMothe |
| 2014/0123990 A1 | 5/2014 | Timmermans |
| 2014/0190502 A1 | 7/2014 | Liu |
| 2014/0196716 A1 | 7/2014 | Liu |
| 2014/0196717 A1 | 7/2014 | Liu |
| 2014/0238422 A1 | 8/2014 | Plunkett et al. |
| 2014/0238424 A1 | 8/2014 | Macko et al. |
| 2014/0261489 A1 | 9/2014 | Cadieux et al. |
| 2014/0261493 A1 | 9/2014 | Smith et al. |
| 2014/0261497 A1 | 9/2014 | Liu |
| 2014/0290653 A1 | 10/2014 | Colomb |
| 2014/0299125 A1 | 10/2014 | Buchberger |
| 2014/0311503 A1 | 10/2014 | Liu |
| 2014/0318538 A1 | 10/2014 | Bilgic |
| 2014/0332019 A1 | 11/2014 | Liu |
| 2014/0334804 A1 | 11/2014 | Choi |
| 2014/0345613 A1 | 11/2014 | Mayer |
| 2014/0360514 A1 | 12/2014 | Zhu |
| 2014/0360517 A1 | 12/2014 | Taggart et al. |
| 2014/0366898 A1 | 12/2014 | Monsees et al. |
| 2014/0376895 A1 | 12/2014 | Han |
| 2015/0020826 A1 | 1/2015 | Liu |
| 2015/0020831 A1 | 1/2015 | Weigensberg et al. |
| 2015/0027457 A1 | 1/2015 | Janardhan et al. |
| 2015/0027461 A1* | 1/2015 | Liu ................. A24F 47/008 131/329 |
| 2015/0027473 A1 | 1/2015 | Graf |
| 2015/0034103 A1 | 2/2015 | Hon |
| 2015/0041558 A1 | 2/2015 | Besseler et al. |
| 2015/0047658 A1 | 2/2015 | Cyphert et al. |
| 2015/0059747 A1 | 3/2015 | Von Schuckmann |
| 2015/0059780 A1 | 3/2015 | Davis et al. |
| 2015/0059782 A1 | 3/2015 | Liu |
| 2015/0059787 A1 | 3/2015 | Qiu |
| 2015/0080808 A1 | 3/2015 | Esteve et al. |
| 2015/0083129 A1 | 3/2015 | Colomb et al. |
| 2015/0090278 A1 | 4/2015 | Schiff et al. |
| 2015/0090279 A1 | 4/2015 | Chen |
| 2015/0090281 A1 | 4/2015 | Chen |
| 2015/0096563 A1 | 4/2015 | Toksoz et al. |
| 2015/0101944 A1 | 4/2015 | Li et al. |
| 2015/0107590 A1 | 4/2015 | Colomb |
| 2015/0114391 A1 | 4/2015 | Colomb et al. |
| 2015/0114393 A1 | 4/2015 | Von Schuckmann |
| 2015/0114408 A1 | 4/2015 | Lord |
| 2015/0128938 A1 | 5/2015 | Colomb et al. |
| 2015/0128967 A1 | 5/2015 | Robinson et al. |
| 2015/0128971 A1 | 5/2015 | Verleur et al. |
| 2015/0128977 A1 | 5/2015 | Li et al. |
| 2015/0136153 A1 | 5/2015 | Lord |
| 2015/0136155 A1 | 5/2015 | Verleur et al. |
| 2015/0144147 A1 | 5/2015 | Li et al. |
| 2015/0150306 A1 | 6/2015 | Chen |
| 2015/0164141 A1 | 6/2015 | Newton |
| 2015/0164142 A1 | 6/2015 | Li et al. |
| 2015/0173124 A1 | 6/2015 | Qiu |
| 2015/0173419 A1 | 6/2015 | Tu |
| 2015/0174346 A1 | 6/2015 | Dhuppad et al. |
| 2015/0181943 A1 | 7/2015 | Li et al. |
| 2015/0196057 A1 | 7/2015 | Wu |
| 2015/0201674 A1 | 7/2015 | Dooly et al. |
| 2015/0208728 A1 | 7/2015 | Lord |
| 2015/0208729 A1 | 7/2015 | Monsees et al. |
| 2015/0208730 A1 | 7/2015 | Li et al. |
| 2015/0216235 A1 | 8/2015 | Liu |
| 2015/0237917 A1 | 8/2015 | Lord |
| 2015/0238723 A1 | 8/2015 | Knudsen |
| 2015/0245654 A1 | 9/2015 | Memari et al. |
| 2015/0245669 A1 | 9/2015 | Cadieux et al. |
| 2015/0257447 A1 | 9/2015 | Sullivan |
| 2015/0272217 A1 | 10/2015 | Chen |
| 2015/0282527 A1 | 10/2015 | Henry, Jr. |
| 2015/0296887 A1 | 10/2015 | Zhu |
| 2015/0297841 A1 | 10/2015 | Ono |
| 2015/0298893 A1 | 10/2015 | Welp |
| 2015/0313287 A1 | 11/2015 | Verleur et al. |
| 2015/0313288 A1 | 11/2015 | Liu |
| 2015/0320116 A1 | 11/2015 | Bleloch et al. |
| 2015/0320947 A1 | 11/2015 | Eicher et al. |
| 2015/0325938 A1 | 11/2015 | Wu |
| 2015/0335072 A1 | 11/2015 | Giller |
| 2015/0335075 A1 | 11/2015 | Minskoff et al. |
| 2015/0342256 A1 | 12/2015 | Chen |
| 2015/0343159 A1 | 12/2015 | Farr et al. |
| 2016/0001011 A1 | 1/2016 | Cammish et al. |
| 2016/0001018 A1 | 1/2016 | Fink et al. |
| 2016/0001019 A1 | 1/2016 | Fink et al. |

(56) References Cited

U.S. PATENT DOCUMENTS

| | | |
|---|---|---|
| 2016/0007654 A1 | 1/2016 | Zhu |
| 2016/0015081 A1 | 1/2016 | Liu |
| 2016/0015082 A1 | 1/2016 | Liu |
| 2016/0015912 A1 | 1/2016 | De Kruijf et al. |
| 2016/0022931 A1 | 1/2016 | Althorpe et al. |
| 2016/0029695 A1 | 2/2016 | Benites et al. |
| 2016/0045684 A1 | 2/2016 | Ono |
| 2016/0050975 A1 | 2/2016 | Worm et al. |
| 2016/0057811 A1 | 2/2016 | Alarcon et al. |
| 2016/0073693 A1 | 3/2016 | Reevell |
| 2016/0073694 A1 | 3/2016 | Liu |
| 2016/0095354 A1 | 4/2016 | Wu |
| 2016/0106155 A1 | 4/2016 | Reevell |
| 2016/0128385 A1 | 5/2016 | Lin |
| 2016/0128386 A1 | 5/2016 | Chen |
| 2016/0135504 A1 | 5/2016 | Li et al. |
| 2016/0143361 A1 | 5/2016 | Juster et al. |
| 2016/0143365 A1 | 5/2016 | Liu |
| 2016/0151589 A1 | 6/2016 | Ohrt et al. |
| 2016/0157523 A1 | 6/2016 | Liu |
| 2016/0158470 A1 | 6/2016 | Esteve et al. |
| 2016/0175547 A1 | 6/2016 | Nakamura |
| 2016/0192707 A1 | 7/2016 | Li et al. |
| 2016/0198765 A1 | 7/2016 | Liu |
| 2016/0198767 A1 | 7/2016 | Verleur |
| 2016/0198771 A1 | 7/2016 | Goggin et al. |
| 2016/0205999 A1 | 7/2016 | Liu |
| 2016/0206005 A1 | 7/2016 | Yamada et al. |
| 2016/0213061 A1 | 7/2016 | Liu |
| 2016/0219934 A1 | 8/2016 | Li et al. |
| 2016/0219936 A1 | 8/2016 | Alarcon |
| 2016/0242466 A1 | 8/2016 | Lord et al. |
| 2016/0264290 A1 | 9/2016 | Hafer et al. |
| 2016/0287818 A1 | 10/2016 | Colomb et al. |
| 2016/0295924 A1 | 10/2016 | Liu |
| 2016/0302487 A1 | 10/2016 | Chen |
| 2016/0309785 A1 | 10/2016 | Holtz |
| 2016/0316817 A1 | 11/2016 | Liu |
| 2016/0338411 A1 | 11/2016 | Liu |
| 2016/0346488 A1 | 12/2016 | Beller |
| 2016/0353800 A1 | 12/2016 | Di Carlo |
| 2016/0353805 A1 | 12/2016 | Hawes et al. |
| 2016/0360794 A1 | 12/2016 | Li et al. |
| 2016/0366936 A1 | 12/2016 | Liu |
| 2016/0366943 A1 | 12/2016 | Li et al. |
| 2016/0367767 A1 | 12/2016 | Cashman et al. |
| 2016/0374390 A1 | 12/2016 | Liu |
| 2016/0374397 A1 | 12/2016 | Jordan et al. |
| 2016/0375207 A1 | 12/2016 | Bhide et al. |
| 2017/0013875 A1 | 1/2017 | Schennum et al. |
| 2017/0013879 A1 | 1/2017 | Frisbee et al. |
| 2017/0027224 A1 | 2/2017 | Volodarsky |
| 2017/0035117 A1 | 2/2017 | Lin |
| 2017/0042228 A1 | 2/2017 | Liu |
| 2017/0056608 A1 | 3/2017 | McDerment et al. |
| 2017/0064999 A1 | 3/2017 | Perez et al. |
| 2017/0071252 A1 | 3/2017 | Liu |
| 2017/0071257 A1 | 3/2017 | Lin |
| 2017/0071258 A1 | 3/2017 | Li et al. |
| 2017/0079329 A1 | 3/2017 | Zitzke |
| 2017/0112193 A1 | 4/2017 | Chen |
| 2017/0119057 A1 | 5/2017 | Liu |
| 2017/0127728 A1 | 5/2017 | Li et al. |
| 2017/0164655 A1 | 6/2017 | Chen |
| 2017/0196273 A1 | 7/2017 | Qiu |
| 2017/0202265 A1 | 7/2017 | Hawes et al. |
| 2017/0208866 A1 | 7/2017 | Liu |
| 2017/0224018 A1 | 8/2017 | Li et al. |
| 2017/0281883 A1 | 10/2017 | Li et al. |
| 2017/0325289 A1 | 11/2017 | Liu |
| 2017/0325504 A1 | 11/2017 | Liu |
| 2018/0007960 A1 | 1/2018 | Suzuki et al. |
| 2018/0020726 A1 | 1/2018 | Alarcon et al. |
| 2018/0035718 A1 | 2/2018 | Liu |
| 2018/0049470 A1 | 2/2018 | Chen |
| 2018/0098575 A1 | 4/2018 | Liu |
| 2018/0116288 A1 | 5/2018 | Hu et al. |
| 2019/0046745 A1 | 2/2019 | Nettenstrom et al. |

FOREIGN PATENT DOCUMENTS

| | | |
|---|---|---|
| CN | 2169987 Y | 6/1994 |
| CN | 300865525 | 9/2007 |
| CN | 300840847 | 10/2008 |
| CN | 300867097 | 12/2008 |
| CN | 201352949 Y | 12/2009 |
| CN | 301347038 S | 12/2009 |
| CN | 301433957 S | 6/2010 |
| CN | 101862038 A | 10/2010 |
| CN | 102264420 A | 11/2011 |
| CN | 102326869 A | 1/2012 |
| CN | 202112305 U | 1/2012 |
| CN | 302012774 S | 3/2012 |
| CN | 202375038 U | 8/2012 |
| CN | 202407080 U | 9/2012 |
| CN | 302216014 S | 12/2012 |
| CN | 202635601 U | 1/2013 |
| CN | 202635602 U | 1/2013 |
| CN | 202635604 U | 1/2013 |
| CN | 103025375 A | 4/2013 |
| CN | 202873793 U | 4/2013 |
| CN | 202907798 U | 5/2013 |
| CN | 202919037 U | 5/2013 |
| CN | 203072893 U | 7/2013 |
| CN | 203152485 U | 8/2013 |
| CN | 103300481 A | 9/2013 |
| CN | 203341007 U | 12/2013 |
| CN | 203353688 U | 12/2013 |
| CN | 203353690 U | 12/2013 |
| CN | 203388269 U | 1/2014 |
| CN | 302926278 S | 1/2014 |
| CN | 203423224 U | 2/2014 |
| CN | 203492795 U | 3/2014 |
| CN | 203538380 U | 4/2014 |
| CN | 203563684 U | 4/2014 |
| CN | 203575649 U | 5/2014 |
| CN | 203608849 U | 5/2014 |
| CN | 203618773 U | 6/2014 |
| CN | 103932402 A | 7/2014 |
| CN | 203676136 U | 7/2014 |
| CN | 203828071 U | 9/2014 |
| CN | 204070522 U | 1/2015 |
| CN | 204070569 U | 1/2015 |
| CN | 204070574 U | 1/2015 |
| CN | 204070577 U | 1/2015 |
| CN | 104544567 A | 4/2015 |
| CN | 104544570 A | 4/2015 |
| CN | 303162040 S | 4/2015 |
| CN | 303192526 S | 4/2015 |
| CN | 204317491 U | 5/2015 |
| CN | 303227659 S | 5/2015 |
| CN | 303417607 | 5/2015 |
| CN | 104720114 A | 6/2015 |
| CN | 204393352 U | 6/2015 |
| CN | 303234670 S | 6/2015 |
| CN | 303250845 S | 6/2015 |
| CN | 303442703 S | 6/2015 |
| CN | 303535276 S | 6/2015 |
| CN | 104770882 A | 7/2015 |
| CN | 104770900 A | 7/2015 |
| CN | 204426686 U | 7/2015 |
| CN | 204444245 U | 7/2015 |
| CN | 204483034 U | 7/2015 |
| CN | 303273075 S | 7/2015 |
| CN | 303279026 S | 7/2015 |
| CN | 303300421 S | 7/2015 |
| CN | 303300422 S | 7/2015 |
| CN | 303322969 S | 8/2015 |
| CN | 303322971 S | 8/2015 |
| CN | 303322985 S | 8/2015 |
| CN | 303341926 S | 8/2015 |
| CN | 303350911 S | 8/2015 |
| CN | 204599338 U | 9/2015 |
| CN | 303361183 S | 9/2015 |

(56) References Cited

FOREIGN PATENT DOCUMENTS

| | | |
|---|---|---|
| CN | 303380240 S | 9/2015 |
| CN | 303380242 S | 9/2015 |
| CN | 303380243 S | 9/2015 |
| CN | 303380252 S | 9/2015 |
| CN | 303417611 S | 10/2015 |
| CN | 204742629 U | 11/2015 |
| CN | 204742641 U | 11/2015 |
| CN | 303470028 S | 11/2015 |
| CN | 204888734 U | 12/2015 |
| CN | 204888743 U | 12/2015 |
| CN | 205030514 U | 2/2016 |
| CN | 205052863 U | 3/2016 |
| CN | 205233463 U | 5/2016 |
| CN | 205233464 U | 5/2016 |
| CN | 205390306 U | 7/2016 |
| CN | 205456062 U | 8/2016 |
| CN | 205512367 U | 8/2016 |
| CN | 205597119 U | 9/2016 |
| CN | 105996131 A | 10/2016 |
| CN | 205624484 U | 10/2016 |
| DE | 95102980001 | 9/1996 |
| DE | 96072850001 | 4/1997 |
| DE | 96072850002 | 4/1997 |
| DE | 499019970001 | 7/1999 |
| DE | 499019970002 | 7/1999 |
| DE | 400039090001 | 8/2000 |
| DE | 401071010001 | 2/2002 |
| DE | 402003030001 | 8/2002 |
| DE | 402093100001 | 3/2003 |
| DE | 402093100002 | 3/2003 |
| DE | 402093100003 | 3/2003 |
| DE | 402093100004 | 3/2003 |
| DE | 402093100005 | 3/2003 |
| DE | 403019480001 | 7/2003 |
| DE | 202013010929 U1 | 12/2013 |
| DE | 96072850003 | 3/2016 |
| DE | 102014014415 B4 | 7/2016 |
| DE | 102015103438 A1 | 9/2016 |
| EA | 201100197 A1 | 3/2012 |
| EA | 201300833 A1 | 3/2014 |
| EA | 019736 B1 | 5/2014 |
| EM | 0001050440001 | 6/2003 |
| EM | 0001050440002 | 6/2003 |
| EM | 0005457690001 | 6/2006 |
| EM | 0007369620001 | 6/2007 |
| EM | 0007369620002 | 6/2007 |
| EM | 0007369620003 | 6/2007 |
| EM | 0007369620004 | 6/2007 |
| EM | 0007369620005 | 6/2007 |
| EM | 0007369620006 | 6/2007 |
| EM | 0007369620007 | 6/2007 |
| EM | 0007369620008 | 6/2007 |
| EM | 0008611410001 | 1/2008 |
| EM | 0015105870001 | 5/2009 |
| EM | 0015105870002 | 5/2009 |
| EM | 0013233070007 | 4/2012 |
| EM | 0013233070008 | 4/2012 |
| EM | 0013233070009 | 4/2012 |
| EM | 0013233070010 | 4/2012 |
| EM | 0013233070011 | 4/2012 |
| EM | 0013233070012 | 4/2012 |
| EM | 0024296960003 | 3/2014 |
| EM | 0024296960004 | 3/2014 |
| EM | 0014157800001 | 7/2014 |
| EM | 0014157800002 | 7/2014 |
| EM | 0014157800003 | 7/2014 |
| EM | 0014157800004 | 7/2014 |
| EM | 0014157800005 | 7/2014 |
| EM | 0014157800006 | 7/2014 |
| EM | 0014157800007 | 7/2014 |
| EM | 0014157800008 | 7/2014 |
| EM | 0014157800009 | 7/2014 |
| EM | 0026967650003 | 5/2015 |
| EM | 0029228640002 | 12/2015 |
| EP | 0105810 A2 | 4/1984 |
| EP | 1946659 B1 | 12/2008 |
| EP | 2460424 A1 | 6/2012 |
| EP | 1496858 B1 | 8/2013 |
| EP | 2801270 A2 | 11/2014 |
| EP | 2875739 A1 | 5/2015 |
| EP | 2875740 A2 | 5/2015 |
| EP | 2888964 A1 | 7/2015 |
| EP | 2989912 A1 | 3/2016 |
| EP | 3039976 A1 | 7/2016 |
| EP | 3075270 A1 | 10/2016 |
| EP | 3117725 A1 | 1/2017 |
| EP | 3135139 A1 | 3/2017 |
| EP | 3155908 A1 | 4/2017 |
| EP | 3248480 A1 | 11/2017 |
| EP | 3289898 A1 | 3/2018 |
| FR | 970852009 | 8/1997 |
| FR | 983203001 | 10/1998 |
| FR | 956833001 | 1/1999 |
| FR | 001967001 | 7/2000 |
| FR | 007595001 | 4/2001 |
| FR | 007595002 | 4/2001 |
| FR | 011038001 | 5/2001 |
| FR | 011152001 | 5/2001 |
| FR | 011154001 | 5/2001 |
| FR | 201125490001 | 7/2011 |
| FR | 201127120001 | 7/2011 |
| FR | 201127120002 | 7/2011 |
| FR | 201127120003 | 7/2011 |
| FR | 2962339 A1 | 1/2012 |
| FR | 20124875012 | 8/2013 |
| FR | 3028384 A1 | 5/2016 |
| FR | 3036022 A1 | 11/2016 |
| FR | 3039039 A1 | 1/2017 |
| GB | 318214 A | 1/1930 |
| GB | 2047060 A | 11/1980 |
| GB | 1029228 | 4/1986 |
| GB | 2048538 | 11/1995 |
| GB | 2055446 | 8/1996 |
| GB | 2075058 | 9/1998 |
| GB | 2093858 | 8/2000 |
| GB | 2093859 | 8/2000 |
| GB | 4020185 | 11/2011 |
| GB | 2515562 A | 12/2014 |
| GB | 4041108 | 6/2015 |
| GB | 2533874 A | 7/2016 |
| IT | 1993MIO0001280003 | 3/1993 |
| IT | 2000TOO0002350001 | 9/2000 |
| IT | 2000TOO0002350003 | 9/2000 |
| IT | 2000TOO0002350004 | 9/2000 |
| IT | 2000TOO0002350006 | 9/2000 |
| IT | 2002TOO0002140001 | 9/2002 |
| IT | 2002TOO0002140002 | 9/2002 |
| IT | 2002TOO0002140003 | 9/2002 |
| IT | 2002TOO0002140004 | 9/2002 |
| JP | S60115227 A | 6/1985 |
| JP | 2003508888 A | 3/2003 |
| JP | D1575098 S | 3/2017 |
| KR | 200464889 Y1 | 2/2013 |
| RU | 2201264 C2 | 3/2003 |
| RU | 74071 U1 | 6/2008 |
| RU | 80751 U1 | 2/2009 |
| RU | 81434 U1 | 3/2009 |
| RU | 2353401 C2 | 4/2009 |
| RU | 87916 U1 | 10/2009 |
| RU | 2382657 C1 | 2/2010 |
| RU | 91861 U1 | 3/2010 |
| RU | 94815 U1 | 6/2010 |
| RU | 103281 U1 | 4/2011 |
| RU | 107026 U1 | 8/2011 |
| RU | 110607 U1 | 11/2011 |
| RU | 110608 U1 | 11/2011 |
| RU | 110643 U1 | 11/2011 |
| RU | 111989 U1 | 1/2012 |
| RU | 115629 U1 | 5/2012 |
| RU | 116018 U1 | 5/2012 |
| RU | 2457870 C2 | 8/2012 |
| RU | 120006 U1 | 9/2012 |
| RU | 2460548 C1 | 9/2012 |
| RU | 121426 U1 | 10/2012 |

(56) References Cited

FOREIGN PATENT DOCUMENTS

| | | |
|---|---|---|
| RU | 121703 U1 | 11/2012 |
| RU | 121706 U1 | 11/2012 |
| RU | 121737 U1 | 11/2012 |
| RU | 122000 U1 | 11/2012 |
| RU | 122254 U1 | 11/2012 |
| RU | 124120 U1 | 1/2013 |
| RU | 125433 U1 | 3/2013 |
| RU | 127628 U1 | 5/2013 |
| RU | 128109 U1 | 5/2013 |
| RU | 129368 U1 | 6/2013 |
| RU | 130225 U1 | 7/2013 |
| RU | 130798 U1 | 8/2013 |
| RU | 2489948 C2 | 8/2013 |
| RU | 132318 U1 | 9/2013 |
| RU | 132353 U1 | 9/2013 |
| RU | 2495682 C1 | 10/2013 |
| RU | 135258 U1 | 12/2013 |
| RU | 135878 U1 | 12/2013 |
| RU | 136964 U1 | 1/2014 |
| RU | 142097 U1 | 6/2014 |
| RU | 142147 U1 | 6/2014 |
| RU | 145495 U1 | 9/2014 |
| RU | 145532 U1 | 9/2014 |
| RU | 2541312 C2 | 2/2015 |
| RU | 2542547 C2 | 2/2015 |
| RU | 2564611 C1 | 10/2015 |
| RU | 2580891 C1 | 4/2016 |
| RU | 164003 U1 | 8/2016 |
| RU | 2593362 C2 | 8/2016 |
| RU | 2597579 C2 | 9/2016 |
| RU | 2598754 C2 | 9/2016 |
| RU | 2602307 C2 | 11/2016 |
| RU | 2603604 C2 | 11/2016 |
| RU | 2603739 C2 | 11/2016 |
| RU | 2605792 C2 | 12/2016 |
| WO | WO-DM264451 | 6/1993 |
| WO | WO-DM0264451 | 6/1996 |
| WO | WO-9912596 A1 | 3/1999 |
| WO | WO-03095005 A1 | 11/2003 |
| WO | WO-2004080216 A1 | 9/2004 |
| WO | WO-2007090268 A1 | 8/2007 |
| WO | WO-2008087161 A1 | 7/2008 |
| WO | WO-2009092520 A1 | 7/2009 |
| WO | WO-2009092653 A1 | 7/2009 |
| WO | WO-2009152651 A1 | 12/2009 |
| WO | WO-2010003480 A1 | 1/2010 |
| WO | WO-2010114504 A1 | 10/2010 |
| WO | WO-2010118644 A1 | 10/2010 |
| WO | WO-2010140841 A2 | 12/2010 |
| WO | WO-2011104829 A1 | 9/2011 |
| WO | WO-2011160932 A1 | 12/2011 |
| WO | WO-2012004512 A1 | 1/2012 |
| WO | WO-2012004514 A1 | 1/2012 |
| WO | WO-2012004518 A1 | 1/2012 |
| WO | WO-2012047181 A1 | 4/2012 |
| WO | WO-2012100523 A1 | 8/2012 |
| WO | WO-2012173322 A1 | 12/2012 |
| WO | WO-2013020220 A1 | 2/2013 |
| WO | WO-2013040193 A2 | 3/2013 |
| WO | WO-2013045582 A2 | 4/2013 |
| WO | WO-2013101558 A1 | 7/2013 |
| WO | WO-2013147492 A1 | 10/2013 |
| WO | WO-2014066730 A1 | 5/2014 |
| WO | WO-2014135224 A1 | 9/2014 |
| WO | WO-2014150773 A1 | 9/2014 |
| WO | WO-2014204417 A1 | 12/2014 |
| WO | WO-2015000183 A1 | 1/2015 |
| WO | WO-2015006838 A1 | 1/2015 |
| WO | WO-2015010310 A1 | 1/2015 |
| WO | WO-2015013891 A1 | 2/2015 |
| WO | WO-2015017971 A1 | 2/2015 |
| WO | WO-2015018120 A1 | 2/2015 |
| WO | WO-2015026081 A1 | 2/2015 |
| WO | WO-2015052513 A2 | 4/2015 |
| WO | WO-2015082560 A1 | 6/2015 |
| WO | WO-2015106434 A1 | 7/2015 |
| WO | WO-2015112750 A1 | 7/2015 |
| WO | WO-2015113743 A1 | 8/2015 |
| WO | WO-2015135213 A1 | 9/2015 |
| WO | WO-2015139985 A1 | 9/2015 |
| WO | WO-2015150068 A1 | 10/2015 |
| WO | WO-2015161406 A1 | 10/2015 |
| WO | WO-2015166239 A1 | 11/2015 |
| WO | WO-2015173303 A1 | 11/2015 |
| WO | WO-2015175022 A1 | 11/2015 |
| WO | WO-2015190810 A1 | 12/2015 |
| WO | WO-2015192377 A1 | 12/2015 |
| WO | WO-2016014652 A1 | 1/2016 |
| WO | WO-2015079198 A8 | 2/2016 |
| WO | WO-2016024083 A1 | 2/2016 |
| WO | WO-2016026756 A1 | 2/2016 |
| WO | WO-2016079410 A1 | 5/2016 |
| WO | WO-2016101200 A1 | 6/2016 |
| WO | WO-2016107764 A2 | 7/2016 |
| WO | WO-2016107767 A1 | 7/2016 |
| WO | WO-2016118005 A1 | 7/2016 |
| WO | WO-2016122417 A1 | 8/2016 |
| WO | WO-2016123779 A1 | 8/2016 |
| WO | WO-2016127401 A1 | 8/2016 |
| WO | WO-2016159784 A9 | 11/2016 |
| WO | WO-2016176800 A1 | 11/2016 |
| WO | WO-2016184247 A1 | 11/2016 |
| WO | WO-2016193365 A1 | 12/2016 |
| WO | WO-2016198266 A1 | 12/2016 |
| WO | WO-2016199135 A1 | 12/2016 |
| WO | WO-2017001817 A1 | 1/2017 |
| WO | WO-2017013130 A1 | 1/2017 |
| WO | WO-DM094223001 | 1/2017 |
| WO | WO-2016033421 A8 | 3/2017 |
| WO | WO-2017037457 A1 | 3/2017 |
| WO | WO-2017064051 A1 | 4/2017 |
| WO | WO-2017081176 A2 | 5/2017 |
| WO | WO-2017109448 A2 | 6/2017 |
| WO | WO-2017163044 A1 | 9/2017 |
| WO | WO-2017163045 A1 | 9/2017 |
| WO | WO-2017163047 A1 | 9/2017 |
| WO | WO-2017163050 A1 | 9/2017 |
| WO | WO-2017163051 A1 | 9/2017 |
| WO | WO-2017163052 A1 | 9/2017 |
| WO | WO-2017176111 A1 | 10/2017 |
| WO | WO-2017191176 A1 | 11/2017 |
| WO | WO-2017206211 A1 | 12/2017 |
| WO | WO-2018000367 A1 | 1/2018 |
| WO | WO-2018015724 A1 | 1/2018 |

OTHER PUBLICATIONS

Decision dated Mar. 14, 2017 for Ukrainian Application No. S201601341, 7 pages.
Decision to Grant dated Aug. 15, 2017 for Russian Application No. 201650539349, 4 pages.
Decision to Grant dated Aug. 28, 2017 for Russian Application No. 201750018449, 4 pages.
Electronic Cigarette | Vype Pebble | Govype, post date n/a, (c)n/a, govype.com, Aug. 30, 2017, https://www.govype.com/uk/vype-pebble-starter-kit. 2 pages.
Examination Report for Canadian Application No. 169756, dated Nov. 17, 2016, 1 page.
Extended Search Report dated Apr. 3, 2017 for European Application No. 13895763.4, 12 pages.
Formalities Notice No. 1 for Australian Design Application No. AU201614224, dated Aug. 9, 2016., 2 pages.
Formalities Notice No. 1 for Australian Design Application No. 201614225, dated Aug. 9, 2016, 2 pages.
Innokin EQ Pod System Vape Kit by vapeclub. dated 2018. found online [Sep. 24, 2018] https://www.vapeclub.co.uk/pods-and-closed-system-vape-starter-- kits/innokin-eq-pod-system-vape-kit.html, 6 pages.
International Preliminary Report on Patentability for Application No. PCT/GB2017/050781, dated Feb. 27, 2018, 13 pages.
International Preliminary Report on Patentability for Application No. PCT/GB2017/050784, dated Jun. 11, 2018, 18 pgs.

(56) References Cited

OTHER PUBLICATIONS

International Preliminary Report on Patentability for Application No. PCT/GB2017/050788, dated Aug. 3, 2018, 14 pages.
International Search Report and Written Opinion for Application No. PCT/CN2013/085455, dated Jul. 24, 2014, 13 pages.
International Search Report and Written Opinion for Application No. PCT/GB2017/050781 dated Jun. 14, 2017.
International Search Report and Written Opinion for Application No. PCT/GB2017/050784, dated Jun. 14, 2017, 10 pgs.
International Search Report and Written Opinion for Application No. PCT/GB2017/050788, dated Jun. 7, 2017, 13 pages.
International Search Report and Written Opinion for Application No. PCT/GB2017/050789, dated Jun. 7, 2017, 9 pages.
International Second Written Opinion for PCT Application No. PCT/GB2017/050788, dated Mar. 7, 2018, 9 pages.
JustFog C601 Pod System Vape Kit by vapeclub. dated 2018. found online [Sep. 24, 2018] https://www.vapeclub.co.uk/pods-and-closed-system-vape-starter-kits/justfog-c601-pod-system-vape-kit.html, 6 pages.
Notice of Allowance for Chinese Application No. 201630632827.4, dated Feb. 24, 2017, 2 pages.
Notice of Allowance for Japanese Application No. 2016016955, dated Feb. 14, 2017, 2 pages.
Notice of Allowance for Japanese Application No. 2016016956, dated Feb. 14, 2017, 2 pages.
Notice of Allowance for Japanese Application No. 2016-523940, dated Sep. 5, 2017, 6 pages.
Notice of Allowance for Japanese Application No. 2017-000313, dated Dec. 19, 2017, 3 pages.
Notice of Issuance for Chinese Application No. 201630370608.3, dated Dec. 30, 2016, 3 pages.
Notification of Transmittal of International Preliminary Report on Patentability for Application No. PCT/CN2013/085455, dated Feb. 2, 2016, 6 pages.
Office Action dated Nov. 28, 2017 for Chinese Application No. 201380080347.5, 8 pages (18 pages with translation).
Office Action for Chinese Application No. 201630370608.3, dated Nov. 1, 2016, 1 page.
Office Action for Japanese Application No. 2017-000313, dated Aug. 29, 2017, 4 pages.
Office Action dated Apr. 27, 2017 for Russian Application No. 2016115006, 2 pages (7 pages with translation).
Office Action dated Feb. 21, 2017 for Russian Application No. 2016505393.
Office Action dated Jan. 13, 2017 for Ukrainian Application No. S201601341, 1 pages.
Office Action dated Nov. 23, 2016 for Mexican Application No. MX/f/2016/002430, 1 pages.
Office Action dated Oct. 6, 2016 for Russian Application No. 2016503052, 2 pages.
Patent Examination Report dated Sep. 22, 2016 for Australian Application No. 2013403212, 5 pages.
Search Report dated Apr. 23, 2020 for Chinese Application No. 201780016823.5, 3 pages.
Search Report dated Aug. 1, 2016 for Great Britain Application No. 1605102.1, 4 pages.
Search Report dated Aug. 11, 2016 for Great Britain Application No. 1605104.7, 5 pages.
Search Report dated Aug. 16, 2016 for Great Britain Application No. 1605103.9, 4 pages.
Search Report dated Aug. 25, 2016 for Great Britain Application No. 1605100.5, 3 pages.
Search Report dated Aug. 3, 2016 for Great Britain Application 1605106.2, 5 pages.
Search Report dated Jun. 1, 2017 for Great Britain Application No. 1613322.5, 3 pages.
Search Report dated Jun. 9, 2017 for Great Britain Application No. 1612684.9, 4 pages.
Smoant S8 Ultra-Portable System Kit _ Premium Electronic Cigarette by wicked vapor, mailed 2018, found online on Sep. 24, 2018, at https://wicked-vapor.com/products/smoant-s8-ultra-portable-system-kit, 2 pages.
Vincent V., "Renova Vapor Zero vape Pod Kit", mailed May 29, 2018, found online on Sep. 24, 2018, https://www.e-cigarette-forum.com/threads/renova-vapor-zero-vape-pod-kit-hqd-comma-vape-pod-kit-wismec-hiflask-pod-kit.865421/.
Application and File History for U.S. Appl. No. 15/029,325, filed Apr. 14, 2016, Inventor: Leadley et al.
suorinusa.Com, *Suroin Drop*, available at https://ww.suornusa.com/collections/suorin-drop, retrieved on Jun. 10, 2020, 8 pages.
Notice of Opposition dated Sep. 7, 2021 for European Application No. 17714516.6 (EP3432958), 27 pages.

* cited by examiner

MECHANICAL CONNECTOR FOR ELECTRONIC VAPOR PROVISION SYSTEM

PRIORITY CLAIM

The present application is a National Phase entry of PCT Application No. PCT/GB2017/050784, filed Mar. 21, 2017, which claims priority from GB Patent Application No. 1605102.1, filed Mar. 24, 2016, and GB Patent Application No. 1613322.5, filed Aug. 2, 2016 which is hereby fully incorporated herein by reference.

TECHNICAL FIELD

The present disclosure relates to an electronic vapor (aerosol) provision system such as an e-cigarette, and the mechanical connection of components thereof.

BACKGROUND

Many electronic vapor provision systems, such as e-cigarettes and other electronic nicotine delivery systems, are formed from two main components, namely a cartomizer and a control unit (battery section). The cartomizer generally includes a reservoir of liquid and an atomizer for vaporizing the liquid. The atomizer is often implemented as an electrical (resistive) heater, such as a coil of wire. The control unit generally includes a battery for supplying power to the atomizer. In operation, the control unit may be activated, for example by detecting when a user inhales on the device and/or when the user presses a button, to provide electrical power from the battery to the heater. This activation causes the heater to vaporize a small amount of liquid from the reservoir, which is then inhaled by the user.

This type of e-cigarette therefore generally incorporates two consumables, firstly the liquid to be vaporized, and secondly power in the battery. Regarding the former, once the reservoir of liquid has been exhausted, the cartomizer may be discarded to allow replacement with a new cartomizer. Regarding the latter, the control unit may provide some form of electrical socket for receiving power from an external source, thereby allowing the battery within the e-cigarette to be re-charged.

The cartomizer and the control unit are typically configured as separable components that can be taken apart and rejoined as required by the user, such as to allow replacement of a disposable cartomizer. Screw threads or bayonet fittings are often utilized to provide a separable connection between the components, but these are not appropriate for every configuration of e-cigarette. Alternative connection arrangements are therefore of interest.

SUMMARY

According to a first aspect of some embodiments described herein, there is provided an electronic vapor provision system comprising a cartridge for storing material heatable to generate an aerosol and a control unit housing a battery to provide electrical power for heating, the cartridge and the control unit separably connectable together by at least one latching element, the latching element comprising a foot, and a leg joined at a first end to the foot by a flexible resilient joint and having a first latch member, the foot anchored within one of the cartridge and the control unit, and the other of the cartridge and the control unit having a second latch member on a surface, and positioned and configured to engage with the first latch member when the cartridge and the control unit are brought together with a substantially linear motion, and disengage with the first latch member when the cartridge and the control unit are pulled apart, the engagement and disengagement enabled by movement of the leg of the latching element about the flexible resilient joint.

According to a second aspect of some embodiments described herein, there is provided a control unit for an electronic vapor provision system, the control unit separably connectable to a cartridge and housing a battery for providing electrical power to generate an aerosol from material stored in a connected cartridge, the control unit comprising: at least one latching element for connecting the control unit to the cartridge, the latching element comprising a foot, and a leg joined at a first end to the foot by a flexible resilient joint and having a first latch member, the foot being anchored within the control unit; and wherein the first latch member is configured to engage with a second latch member defined on a surface of a cartridge when the control unit and the cartridge are brought together with a substantially linear motion, and disengage with the second latch member when the control unit and the cartridge are pulled apart, the engagement and disengagement enabled by movement of the leg of the latching element about the flexible resilient joint.

According to a third aspect of some embodiments described herein, there is provided a cartridge for an electronic vapor provision system, the cartridge separably connectable to a control unit and configured to store material heatable to generate an aerosol when heated using electrical power from a battery housed in a connected control unit, the cartridge comprising: at least one latch member having the form of a protrusion or a recess defined on a surface of the cartridge, the latch member configured to engage with a further latch member on a leg of a latching element anchored in a control unit when the cartridge and the control unit are brought together with a substantially linear motion, and disengage from the further latch member when the cartridge and the control unit are pulled apart, the engagement and disengagement enabled by movement of the leg of the latching element about a flexible resilient joint between the leg and a foot of the latching element by which the latching element is anchored in the control unit.

According to a fourth aspect of some embodiment described herein, there is provided a latching element for separably connecting components of an electronic vapor provision system, and comprising: a foot; and a leg joined at a first end to the foot by a flexible resilient joint and having a first latch member; wherein the foot is configured to be anchored within a first component of an electronic vapor provision system, and the latch member is configured to engage with a further latch member defined on a surface of a second component of an electronic vapor provision system when the first and second components are brought together with a substantially linear motion, and disengage with the second latch member when the first and second components are pulled apart, the engagement and disengagement enabled by movement of the leg about the flexible resilient joint.

According to a fifth aspect of some embodiments described herein, there is provided an electronic cigarette comprising a cartomizer housing an aerosol source and a control unit housing a battery, wherein the cartomizer and the control unit are mechanically connectable together, and the control unit comprises at least one latching element, the latching element comprising a foot, and a leg joined to the foot by a flexible resilient joint and having a first latch member, the foot secured within the control unit; and the cartomizer having a surface shaped to define at least one second latch member positioned and configured to engage with a first latch member when the cartomizer and the control unit are brought together with a linear motion and to disengage with the first latch member when the cartomizer and the control unit are pulled apart, the engagement and disengagement enabled by movement of the leg of the latching element about the flexible resilient joint.

These and further aspects of certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, a electronic vapor provision system may be provided in accordance with approaches described herein which includes any one or more of the various features described below as appropriate.

BRIEF DESCRIPTION OF THE DRAWINGS

Various embodiments will now be described in detail by way of example only with reference to the accompanying drawings in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to aerosol provision systems, also referred to as vapor provision systems, such as e-cigarettes. Throughout the following description the term "e-cigarette" or "electronic cigarette" may sometimes be used; however, it will be appreciated this term may be used interchangeably with aerosol (vapor) provision system and electronic aerosol (vapor) provision system.

Figure 1:
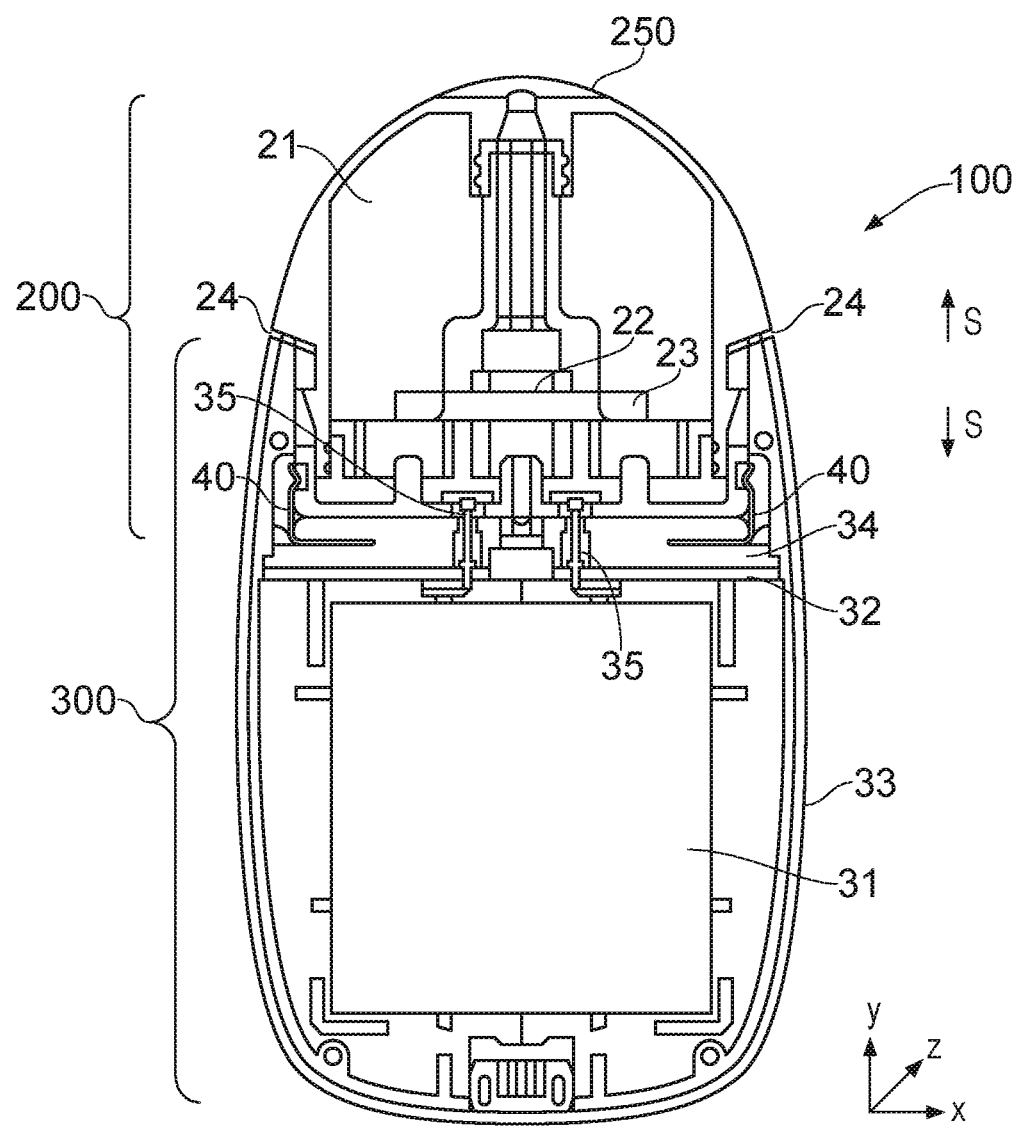
FIG. 1 shows a cross-sectional side view of an example electronic cigarette according to some embodiments described herein.

FIG. 1 is a cross-sectional view through an example e-cigarette 100 in accordance with some embodiments of the disclosure. The e-cigarette 100 comprises two main components, namely a cartomizer 200 and a control unit 300. The cartomizer 200 includes a chamber or reservoir 21 containing a supply of liquid, a heater 22 to act as an atomizer or vaporizer, and a mouthpiece 250. The liquid in the reservoir 21 (sometimes referred to as the e-liquid or source liquid) typically includes nicotine in an appropriate solvent, and may include further constituents, for example, to aid aerosol formation, and/or for additional flavoring. The cartomizer 200 further includes a wick 23 or similar facility to transport a small amount of liquid from the reservoir 21 to a heating location on or adjacent the heater 22. The combination of a wick and a heater may be referred to as an atomizer or vaporizer. The control unit 300 includes within a housing 33 a re-chargeable cell or battery 31 to provide power to the e-cigarette 100 and a printed circuit board 32 (PCB) for generally controlling the e-cigarette. When the heater 22 receives power from the battery 31, as controlled by the PCB 32, the heater 22 vaporizes the liquid from the wick 23 and this vapor is then inhaled by a user through the mouthpiece 250.

For ease of reference, x and y axes are included in FIG. 1. The x axis corresponds to the width of the device 100 (from side to side as shown in FIG. 1), while the y axis corresponds to the height of the device 100 (top to bottom as shown in FIG. 1), where the cartomizer 200 represents an upper portion of the e-cigarette 100 and the control unit 300 represents a lower portion of the e-cigarette 100. Additionally, there is a z axis which is perpendicular to the x and y axes shown in FIG. 1 (into the plane of the Figure). The z axis corresponds to the depth or thickness of the device 100. In this example, the depth of the e-cigarette 100 is significantly less than the width of the e-cigarette 100, resulting in a generally flat or planar configuration (in the x-y plane). Accordingly, the z axis can be considered as extending from face to face of the e-cigarette 100, where one face may be regarded (arbitrarily) as the front face of the e-cigarette 100 and the opposing face as the back face of the e-cigarette 100, the front and back faces being substantially parallel to the plane of FIG. 1.

The cartomizer 200 and the control unit 300 are detachable from one another by separation in a direction parallel to the y-axis (which might be considered as a longitudinal axis of the device 100), indicated in FIG. 1 by the arrows S, but are joined together (as in FIG. 1) when the device 100 is in use so as to provide mechanical and electrical connectivity between the cartomizer 200 and the control unit 300. Hence, the cartomizer 200 and the control unit 300 are separably connectable; they can be joined (coupled) together or separated apart according to user need. When the e-liquid in the cartomizer reservoir 21 has been depleted, the cartomizer 200 is removed and a new cartomizer is attached to the control unit 300. Accordingly, the cartomizer 200 may sometimes be referred to as a disposable portion of the e-cigarette 100, while the control unit 300 represents a re-usable portion. Alternatively, the cartomizer 200 may be configured to be refillable with e-liquid, and may require detachment from the control unit 300 for access to a filling port.

The e-cigarette 100 also includes a sealing member or seal 34 disposed between the cartomizer 200 and the control unit 300 when the two components are connected. For ease of assembly, in this example the seal 34 is disposed within the control unit 300, over the PCB 32 (or other part which may be arranged at the upper face of the control unit 300 in alternative configurations). Alternatively, a seal 34 may be comprised within the cartomizer 200, over its lower face so as come against the PCB 32 when the two components are coupled together. The seal 34 is fabricated from a resilient compressible material such as rubber, sponge, cork or a flexible plastic, and sized so as to undergo at least a small amount of compression when the cartomizer 200 and the control unit 300 are joined together. It is compressed between the upper face of the control unit 300 and the lower face of the cartomizer 200, and extends to the interior of the side walls of the control unit housing 33. This provides a secure and close fit between the components so as to restrict the flow of air to its intended path within the e-cigarette 100 (which is not described further herein). The seal 34 has through-apertures to receive conductive connectors 35 that provide electrical connection between the control unit 300 and the cartomizer 200 when coupled together.

Other components shown in FIG. 1 are not discussed in more detail here since they are not directly related to implementation of embodiments of the disclosure.

Figure 2:
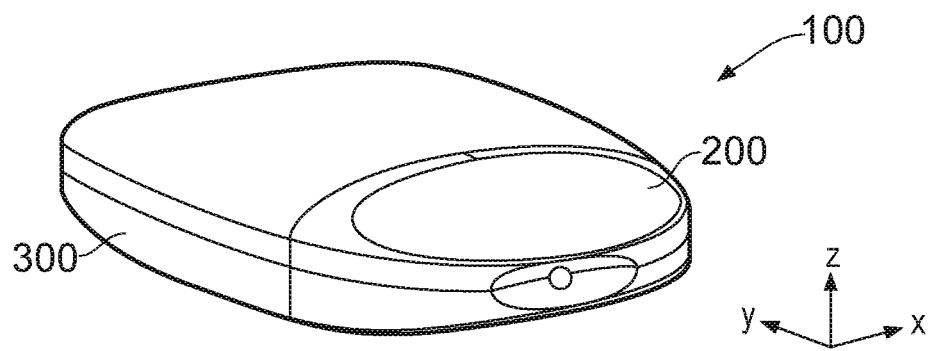
FIG. 2 shows an external perspective view of the example electronic cigarette of FIG. 1.

FIG. 2 is an external perspective view of the e-cigarette 100 of FIG. 1, in its assembled configuration with the cartomizer 200 coupled to the control unit 300 so that the e-cigarette 100 is ready for use. The orientation is different from FIG. 1, as indicated by the xyz axes.

Figure 3:
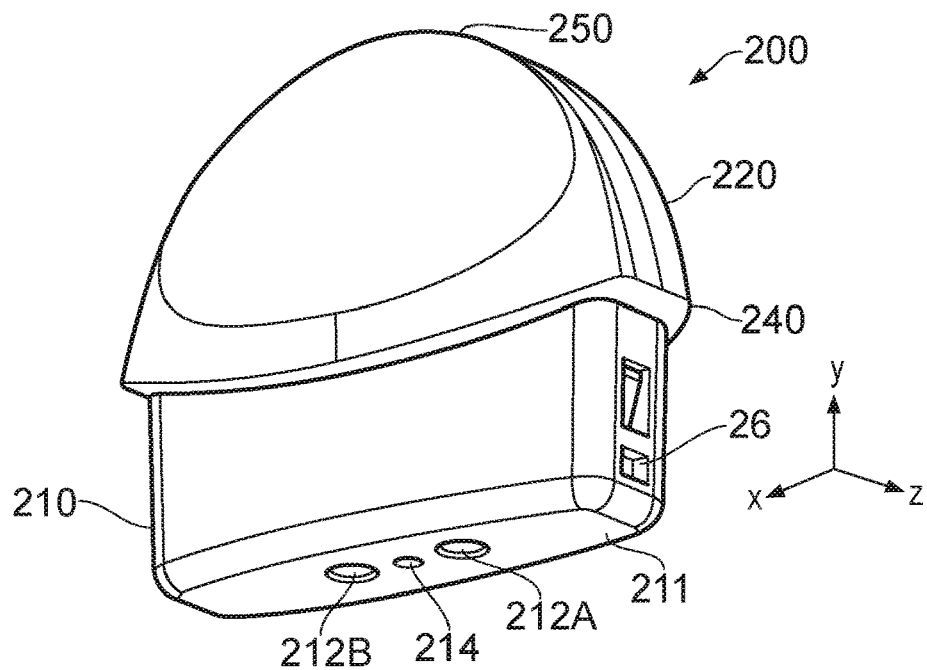
FIG. 3 shows an external perspective view of a cartomizer section of the example electronic cigarette of FIG. 2.

FIG. 3 is a perspective external view of the cartomizer 200 of the e-cigarette 100 of FIG. 1 in accordance with some embodiments of the disclosure. Together with FIG. 2, this external view confirms that the depth of the cartomizer 200 (and the e-cigarette 100 as a whole), as measured parallel to the z axis, is significantly less than the width of the cartomizer 200 (and the e-cigarette 100 as a whole), as measured parallel to the x axis. More generally, the e-cigarette 100 has a non-circular cross-section in the x-z plane, orthogonal to the y-axis and the direction of separation, at the location of the separable join between the cartomizer 200 and the control unit 300.

The cartomizer 200 comprises two main portions (at least from an external viewpoint). In particular, there is a lower or base portion 210 and an upper portion 220. The upper portion 220 is shaped to provide the mouthpiece 250 of the e-cigarette 100. When the cartomizer 200 is assembled with the control unit 300, the base portion 210 of the cartomizer 200 sits within the upper part of the housing 33 of the control unit 300, and hence is not externally visible, whereas the upper portion 220 of the cartomizer 200 protrudes above the control unit 300, and hence is externally visible. Accordingly, the depth and width of the base portion 210 are smaller than the depth and width of the upper portion 220, to allow the base portion 210 to fit inside the control unit 300. The increased depth and width of the upper portion 220 compared with the base portion 210 is provided by a lip or rim 240. When the cartomizer 200 is inserted into the control unit 300, this lip or rim 240 abuts against the top edge of the control unit housing 33.

As also shown in FIG. 3, the base portion 210 has a lower face defined by a bottom wall 211. This face abuts and compresses the sealing member 34 when the cartomizer 200 is connected to the control unit 300. The bottom wall 211 includes two larger holes 212A, 212B on either side of a smaller hole 214 which is for air inlet into the cartomizer interior. The larger holes 212A and 212B are used to accommodate positive and negative electrical connections from the control unit 300 to the cartomizer 200, provided by the conductive connectors 35 shown in FIG. 1. The larger holes 221A, B are aligned with the through-apertures in the sealing member 34. When a user inhales through the mouthpiece 250 and the device 100 is activated, air flows into the cartomizer 200 through the air inlet hole 214 (via a pathway leading from ventilation slots 24 (see FIG. 1) defined at the juncture between the top edge of the control unit housing 33 and the cartomizer lip 240). This incoming air flows past the heater 22 (not visible in FIG. 3), which receives electrical power from the battery 31 in the control unit 300 so as to vaporize liquid from the reservoir 21 (and more especially from the wick 23). This vaporized liquid is then incorporated or entrained into the airflow through the cartomizer 200, and hence is drawn out of the cartomizer 200 through mouthpiece 250 for inhalation by the user.

The flattened, planar shape of the e-cigarette 100 is in contrast to many known e-cigarette devices which have a generally cylindrical shape. In any two-part e-cigarette comprising a separable cartomizer and control unit, it is necessary to provide a mechanical connection which engages when the two components are brought into conjunction and acts to retain the components in the connected position. Devices of a cylindrical shape frequently use a connection arrangement that relies on a rotatory motion between the two components, such as a screw thread or a bayonet fitting. The flattened non-circular shape of the e-cigarette 100 makes a rotatable connection less practical and more complex. Consequently, the e-cigarette 100 uses an alternative connection arrangement to mechanically couple the cartomizer 200 to the control unit 300, that uses a linear movement.

To this end, the e-cigarette 100 comprises a pair of latching elements 40. These are labeled in FIG. 1, but can be seen more clearly in FIG. 4, which is an enlarged view of the upper part of FIG. 1. The two latching elements 40 are oppositely disposed, one on each side of the e-cigarette 100, within the housing 33 of the control unit 300.

Figure 5:
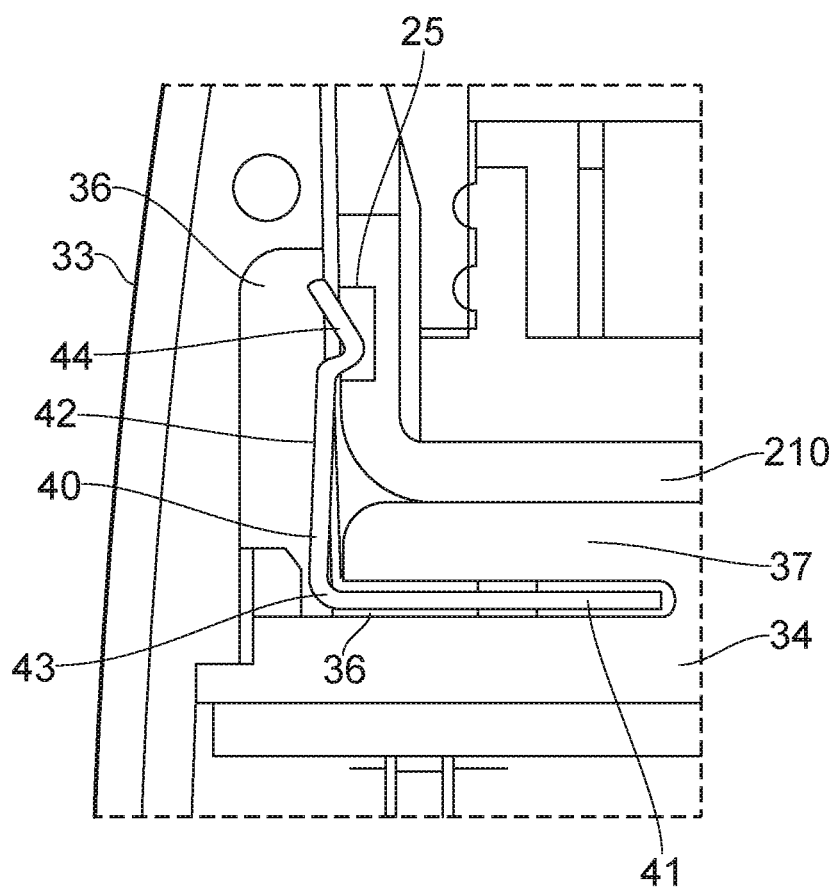
FIG. 5 shows an enlarged view of part of FIG. 4, including a first example latching element.

FIG. 5 is a further enlarged view of part of FIG. 1, showing one of the latching elements 40 (first latching element) with its adjacent parts when the cartomizer 200 and the control unit 300 are coupled together. The latching element 40 comprises a foot part 41 and a leg part 42. The foot 41 and the leg 42 meet at a resilient flexible joint or junction 43. In the current example, the foot 41 and the leg 42 are substantially linear elongate elements arranged substantially at 90 degrees to each other. The flexibility of the junction 43 between the foot 41 and the leg 42 allows one to move with respect to the other, in particular in a hinged-type movement to increase or decrease the separating angle, when an external force is applied to the leg 42. The resilience of the junction 43 returns the angle to its original size when the force is removed, maintaining the usual shape of the latching element.

The latching element 40 is secured to the control unit 300 so that the leg 42 extends beyond the upper face of the control unit 300, in this example defined by the surface of the sealing element 34. In the FIG. 5 embodiment, the latching element 40 may be secured by anchoring the foot part 41 within the seal 34. The foot part 41 lies generally in the plane of the seal 34 (the x-z plane from FIG. 1), while the leg part 42 extends along the y-axis. The seal 34 is shaped to receive the foot part 41, for example there is a hole 36 extending from the side edge of the seal 34 into the body of the seal 34 into which the foot part is inserted, and/or the seal 34 is formed with a tongue or flange portion 37 parallel to the plane of the seal 34 under which the foot part 41 is lodged. Compression of the seal 34 when the e-cigarette 100 is assembled may act to hold the latching element 40 firmly in place, since a hole will be squeezed closed and a tongue will be depressed against the underlying part of the seal 34. Alternatively, if the seal 34 is made of an appropriate textured and structured material, the foot part 41 may be inserted directly into the body of the seal 34 without any prior formation of a hole, tongue or other receiving recess.

Alternatively, the seal 34 may be shaped to receive the foot part 41 for the purpose of accommodating the latching element 40 within the control unit 300, rather than for anchoring or otherwise securing the latching element 40 in place. In such an example, there is no reliance on compression of the seal 34 to grip and hold the latching element 40. Instead, the latching element 40 may be secured to a different part or parts of the control unit 300, for example directly to the housing 33. For example, there may be molded or shaped parts formed from rigid plastic (such as on the housing 33) which engage around the foot part 41 to house it and hence hold it in place. Alternatively, the foot part 41 may be anchored by screws or rivets attached through the latching element 40 and into the control unit 300, or by being glued or welded to the control unit 300. Furthermore, in instances where the seal 34 does not perform any anchoring function, it is optional whether the seal 34 is shaped to accommodate the foot part 41; depending on the location of the latching element 40 and the technique used to anchor it, shaping of the seal 34 in this regard may not be required.

The leg part 42 of the latching element 40 has a shaped latch member 44 formed at, near or towards its end opposite the flexible junction 43. The latch member 44 is provided to cooperatively engage with a further latch member 25 formed on the exterior side wall of the cartomizer 200. In this example the latch member 44 is a protrusion from the surface of the leg part 42.

Figure 4:
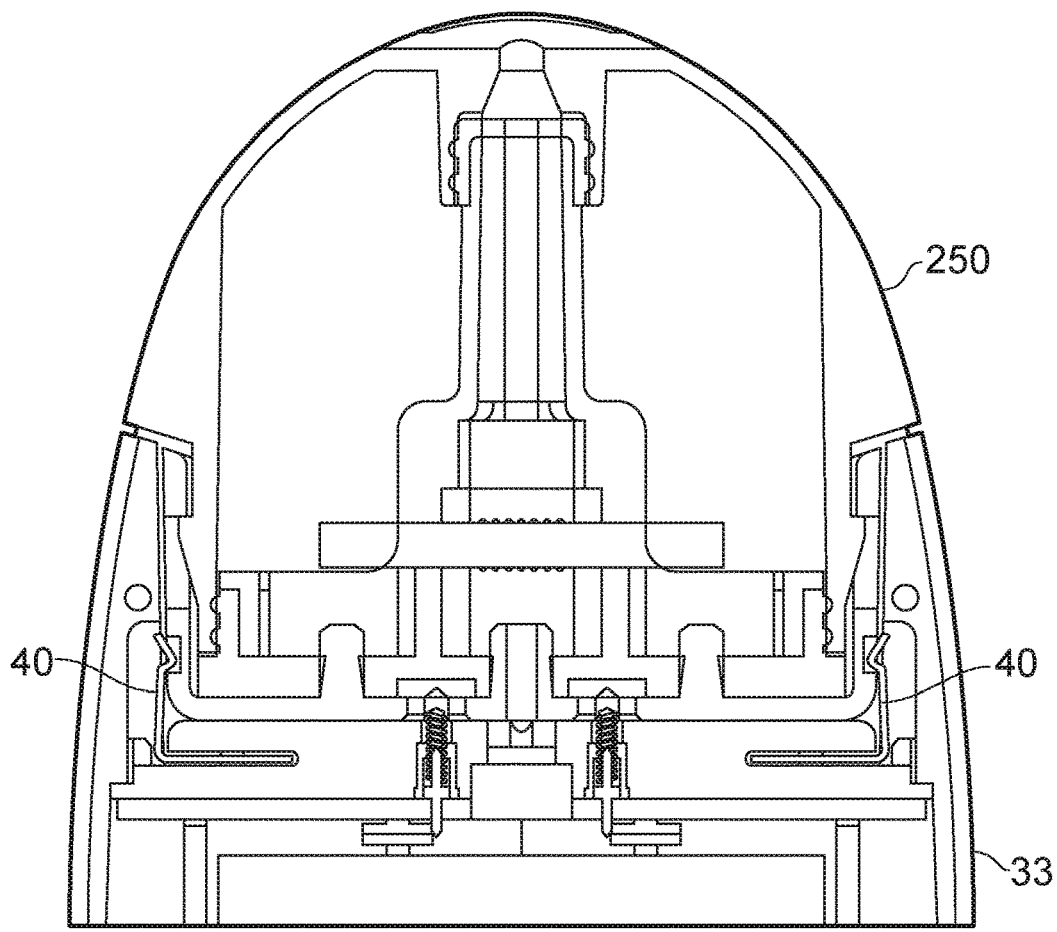
FIG. 4 shows an enlarged view of an upper part of FIG. 1.

Returning to FIG. 3, it will be seen that the cartomizer base portion 210 includes in its side wall a recess, notch or indentation 26. This forms the further latch member 25 in this example, and is positioned to align with the latching element latch member 44 when the cartomizer 200 and control unit 300 are fully engaged together. The recess 26 receives the corresponding protrusion 44. The opposite side wall of the base portion 210 is provided with a similar notch or indentation to likewise receive the latch member 44 of the second latching element 40, arranged opposite the first latching element in the seal 34 as shown in FIG. 4.

As the cartomizer 200 and the control unit 300 are brought together, for example by pushing the base portion 210 of the cartomizer 200 into the top of the control unit 300, the base portion 210 meets the latch members 44 of the two latching elements 40 which protrude so as to have a spacing less than the width of the base portion 210. The force of the incoming cartomizer 200 pushes against the latching elements 40, and the flexibility of the resilient joints 43 causes the joints to extend and allow the leg parts 42 to move outwards to accommodate the base portion 210. When the cartomizer 200 has been inserted to its intended position, the latch members 44 are in line with the recesses 26 in the base portion 210, the side walls of the base portion 210 no longer act on the latch members 44, and the resilient joints 43 are able to flex back to their original positions, bringing the protruding latch members 44 into the recesses 25. The latch members 44 are thereby engaged with the recesses 25, and securely retain the cartomizer 200 within the control unit 300 during operation of the device 100. It will be appreciated that the latching elements 40 operate to provide a "snap fit" connection, enabled by a relative linear motion between the cartomizer 200 and the control unit 300. The two components are brought together along a line, and no rotation is needed to effect the coupling. The connection is adequately secure to withstand everyday usage of the e-cigarette 100, but can be overcome by deliberately pulling the cartomizer 200 and the control unit 300 apart along the y-axis (again, a linear movement). This will cause the base portion side walls to force the leg parts 42 outwards again, moving the latch members 44 out of the recesses 25 and allowing the cartomizer 200 to be separated from the control unit 300.

Note that in this example, the housing 33 of the control unit extends in the y-direction past the leg parts 42 of the latching element 40, forming the upper part of the housing 33 into which the base portion 210 of the cartomizer 200 is inserted. A cavity 36 is provided in the inside of the housing 33 adjacent to the leg part 42, to accommodate the leg part 42 when it is moved outwards by the force exerted by the base portion 210.

Figure 6:
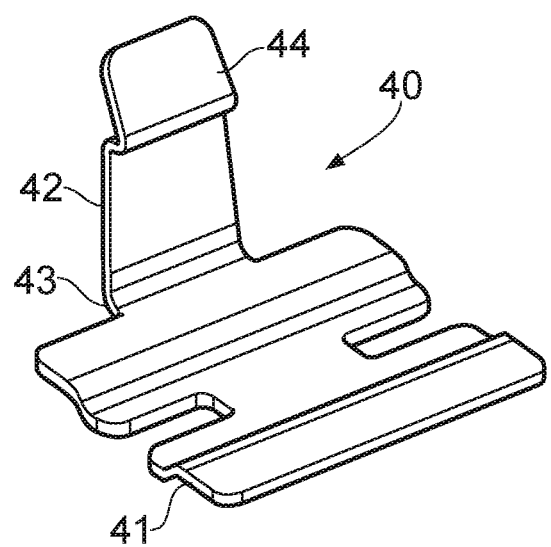
FIG. 6 shows a perspective view of an example latching element.

FIG. 6 shows a perspective view of an example latching element 40, of the type from the FIG. 5 example. From this it can be seen that the foot part 41 has a greater depth (z-direction) than the leg part 42 and the joint 43. This arrangement may facilitate a secure anchoring of the foot part 41 by providing a larger surface area to be received in the compressed seal 34 or secured to the housing 33, while allowing flexion/extension of the joint 43 with small or moderate force. Indeed, the depth of the foot 41 may be as much as the full depth of the interior of the control unit 300, or may be less. Also, these proportions are examples only, and the foot 41 and leg 42 may be the same or similar depth. The joint 43 alone may have a reduced depth compared to the foot 41 and leg 42, or may be the same or greater depth than either or both the foot 41 and the leg 42. (Considering the latching element 40 alone, without reference to the dimensions and axes defined for the e-cigarette 100 as whole, the "depth" just discussed may more intuitively be considered as a width. It is a dimension parallel to the direction about which the hinging or rotating action of the joint 43 operates.)

The latching element 40 may be made from any material able to provide the flexible resilient character of the joint 43 between the leg 42 and the foot 41. For example, the latching element 40 may be made from metal, for example from stainless steel. For example, it may be made by stamping or cutting a flat shape from sheet metal, and forming the required angled shapes of the joint 43 and the latch member 44 by pressing or bending the flat shape with a die. Purely as an example, the latching element 40 may be stamped from a sheet of stainless steel of 0.3 mm thickness, to have a formed size of 9 mm by 9 mm (dimensions of the foot 41) by 7 mm high (length of the leg 42). As other examples, the thickness of the material (stainless steel or otherwise) may be in the range of 0.1 mm to 0.7 mm, and the foot 41 may have dimensions in the range of 5 mm to 15 mm by 5 mm to 15 mm (it need not be square), with a leg 42 of length in the range 5 mm to 12 mm. Dimensions outside these ranges are also contemplated, and will depend in part on the space available to accommodate the latching element 40 and the properties of the material from which is made. A molded plastics latching element 40 could provide the required resilient, flexible properties. For a molded formation, the protruding latch member 44 can be a solid shape extending from surface of the leg 42, rather than a hollow shape such as is formed by bending (as in the FIG. 6 example). Conveniently, the latching element 40 is integrally formed as a single part from a single material, e.g. comprising a plastics or metallic or other suitable material.

The example e-cigarette 100 described thus far has a pair of latching elements 40 disposed on opposite sides of the control unit 30. More than two latching elements 40 may be provided if desired, and the latching elements 40 may be positioned anywhere around the perimeter of the e-cigarette 100. Alternatively, it may be found that a sufficiently secure mechanical coupling can be achieved with a single latching element 40.

Figure 7:
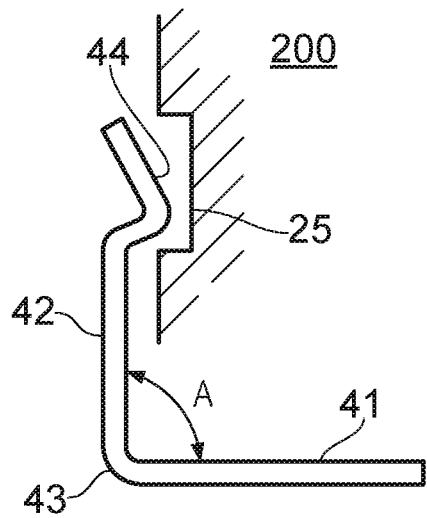
FIG. 7 shows a schematic side view of an example latching element.

FIG. 7 shows a schematic side view of a latching element 40 of similar shape to that in FIG. 6. The leg 42 and foot 41 are positioned substantially at right angles, separated by an angle A of substantially 90 degrees. Hence the latching element 40 is generally L-shaped. If mounted in an e-cigarette 100 according to the FIG. 5 example, namely so that the foot 41 points inwardly towards a central longitudinal axis of the e-cigarette 100 (being the axis along which the cartomizer 200 and/or control unit 300 are moved for connection and separation) and faces the same direction as the latch member 44, the latching element 40 will bend to perform its latching action firstly by an increase in angle A (the joint 43 extends and the leg 42 moves outwards away from the central axis), and then a decrease in angle A back to its original size (the joint 43 flexes and the leg 42 moves back towards the central axis to insert the latch member 44 into the recess on the cartomizer 200).

Figure 8:
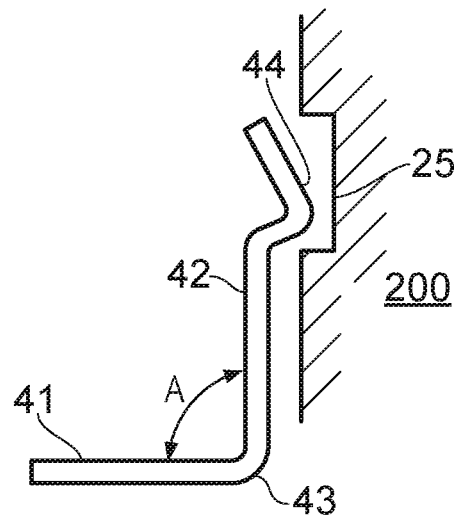
FIG. 8 shows a schematic side view of a further example latching element

FIG. 8 shows a schematic side view of an alternative latching element 40 which is configured to be mounted in an opposite orientation to that of FIG. 7, namely with its foot 41 pointing outwardly away from the central axis of the e-cigarette 100 and facing the opposite direction from the latch member 44. This can be enabled by, for example, an alternative shaping of the seal 34 or by anchoring the foot 41 into the side wall of the control unit housing 33. In this case, the angle A of the joint 43 (again substantially 90 degrees between the leg 42 and foot 41) firstly decreases to bring the leg 42 outwards, and then increases back to its original size to bring the leg 42 back towards the axis and insert the latch member 44 into the recess in the cartomizer 200.

Also, the angle between the leg 42 and the foot 41, being the "rest" position of the joint 43 when no forces are acting on the latching element 40 to rotate either the leg 42 or the foot 41 about the joint 43, need not be 90 degrees, but may be more or less than 90 degrees. An angle of 90 degrees or close to it may be preferred, for example an angle in the range of 88 degrees to 92 degrees. A larger difference from 90 degrees may be tolerated in certain configurations, and depending on size and shape of the volume available to accommodate the latching elements 40, for example in the range 85 degrees to 95 degrees, or 80 degrees to 100 degrees, or 70 degrees to 110 degrees.

Figure 9:
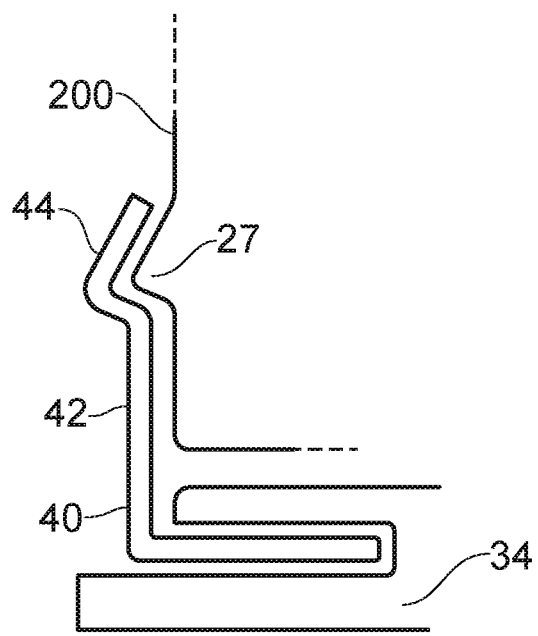
FIG. 9 shows a schematic side view a still further example latching element.

As a further alternative, the respective latch members 44 of the latching element 40 and the cartomizer 200 may be oppositely configured, so that the latch member 44 of the latching element 40 has a recessed shape and the latch member 44 on the cartomizer 200 has a protruding shape. FIG. 9 shows an example latching element 40 configured in this way. The latch member 44 at the upper end of the leg 42 is formed by bending the sheet metal (or molding the plastic) in the opposite shape from the FIG. 7 example, so that the leg surface intended to face the cartomizer 200 is recessed or indented. The cartomizer 200, for example on the side wall of its lower portion 210 if configured similarly to FIG. 3, has a corresponding protrusion 27 shaped and sized to fit into the indent of the latch member 44. More generally, the cooperating latch members 44 are a cooperating engageable pair comprising a concavity (aperture, recess, hole, indention, notch) and a convexity (protrusion, lug), where the convexity can at least partly engage into the concavity. It is immaterial which of the latching element 40 and the cartomizer 200 has the convexity and which the concavity. Furthermore, more complicated engageable shapes may be used, for example with each of the latch members 44 comprising both some concavity and some convexity.

Moreover, the latching arrangement as a whole may be oppositely arranged, with one or more latching elements 40 anchored (secured, mounted) on the cartomizer 200, and the corresponding further latch members 44 (concave or convex) provided on an appropriate surface of the control unit 300.

Figure 10:
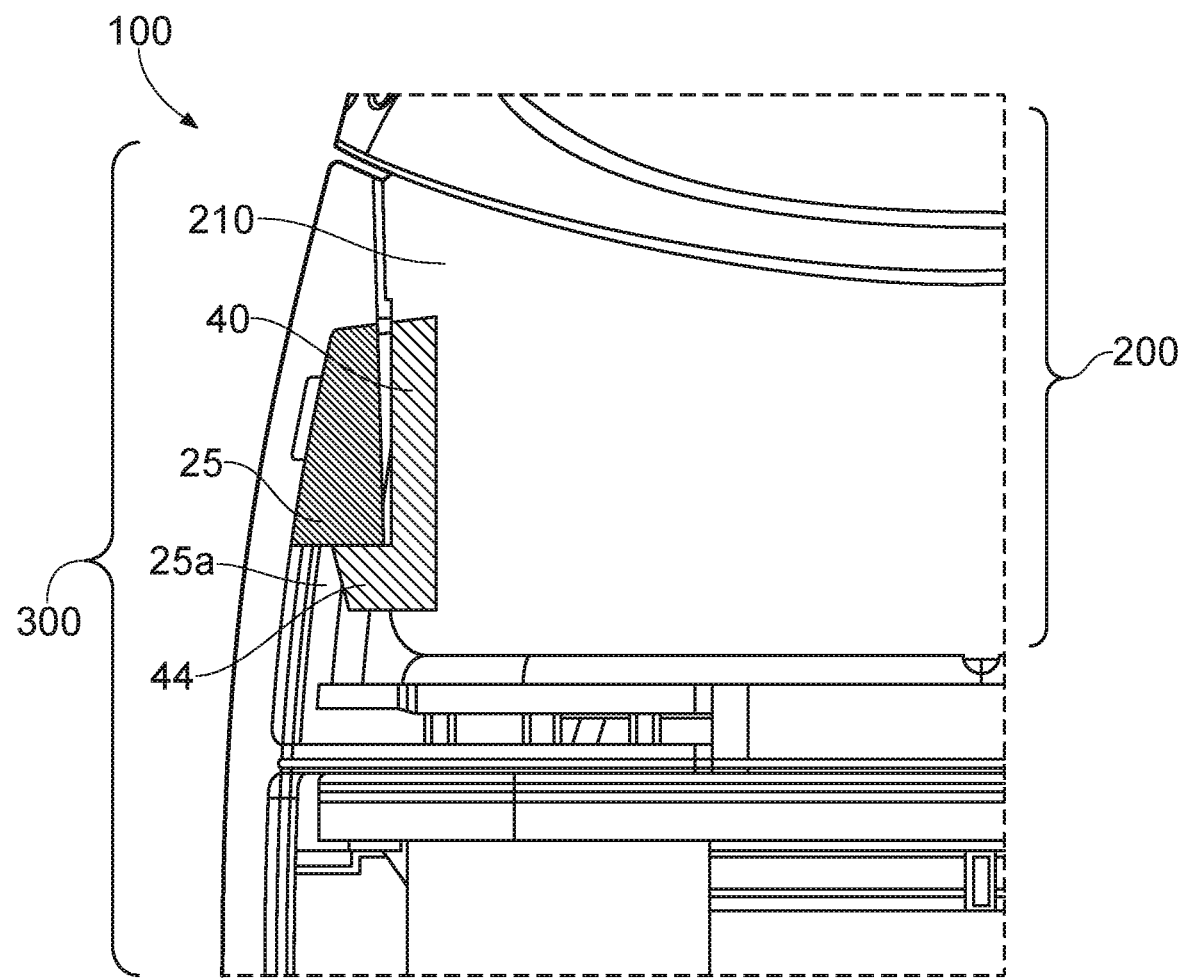
FIG. 10 shows an enlarged cross-sectional view of part of an example electronic cigarette with a further example latching element.

FIG. 10 shows a cross-sectional view of part of an example e-cigarette 100 configured in this way. Shown in a highly schematic form (and therefore not suggesting any limitations on the shape and format of the latching element 40 and the latch members 44) are a latching element 40 secured to the base portion 210 of the cartomizer 200 so that its latch member 44 faces outwardly towards the side wall of the control unit 300. A cooperating latch member 25 is provided facing inwardly from the control unit side wall. The latch member 25 protrudes from the side wall and hence defines a cavity 25a beneath itself. This provides a recess or concavity to receive the protruding convex lug of the latching element latch member 44. In other examples, a latching member anchored to the cartomizer 200 may have a concave latch member and the control unit 300 may carry a convex latch member, such as in the FIG. 9 example.

As discussed with reference to FIG. 3, in some example e-cigarettes 100 the cartomizer 200 has a lower or base portion which, in the assembled e-cigarette 100, sits within an upper part of the control unit housing 33. The upper part of the control unit housing 33 is formed as an upstanding wall defining a recess or cavity into which the base portion of the cartomizer 200 is inserted to make the latching connection. The cavity and the base portion might be shaped for a very close fit, but for ease of insertion and subsequent detachment it may be useful for a small spacing or gap to be provided between the opposing surfaces of these two parts. With such a configuration, the latching elements will secure the cartomizer 200 and control unit 300 firmly together in the longitudinal direction (along the direction of linear motion used to achieve latching), but the spacing may allow a small amount of movement or "play" between the cartomizer 200 and the control unit 300 in other directions even when they are securely latched together. To address this, protrusions or bumps may be provided on one or more of the opposing surfaces.

Figure 11:
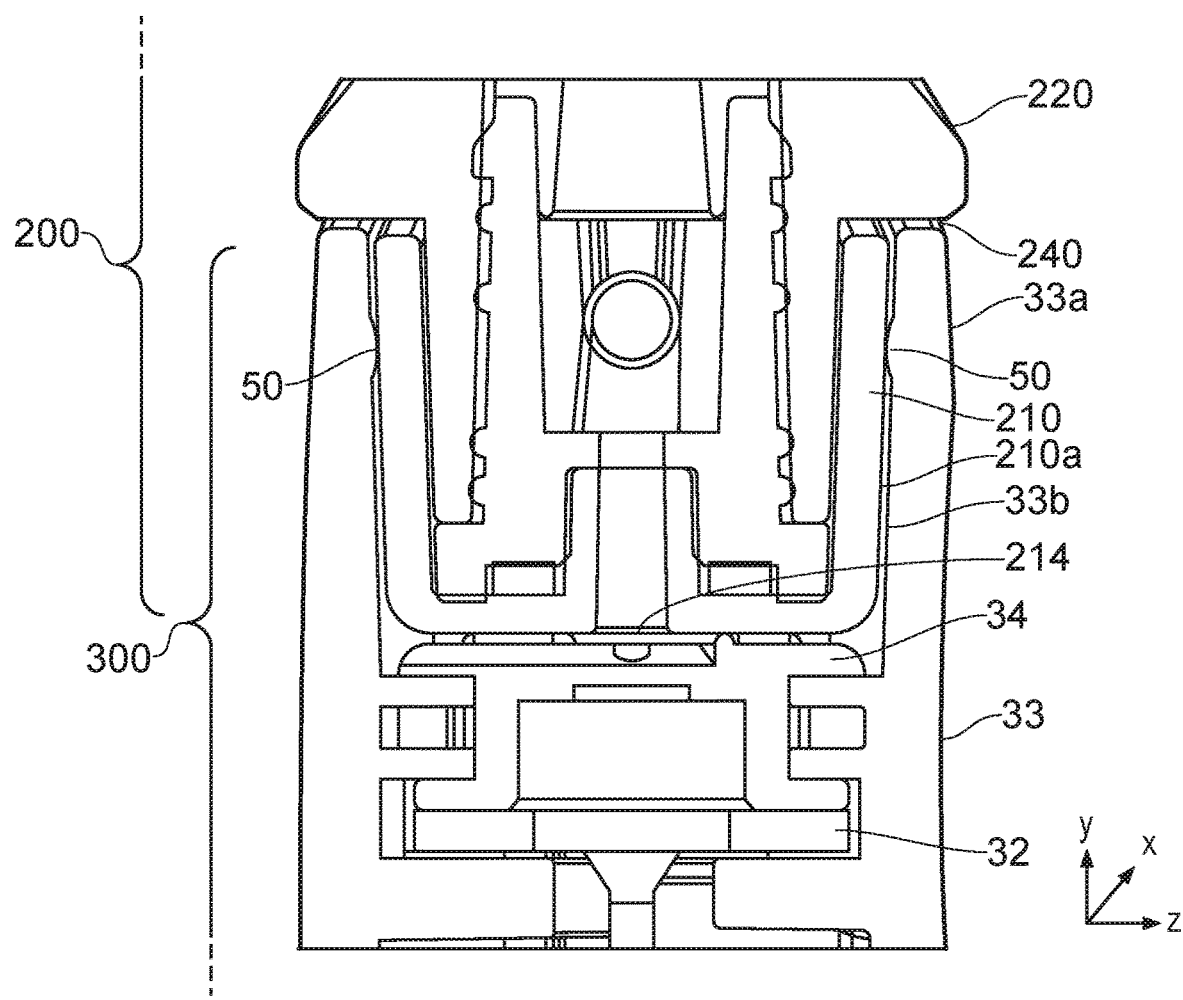
FIG. 11 shows a cross-sectional view of part of further example electronic cigarette according to some embodiments.

FIG. 11 shows a cross-sectional view through a mid-part of an example e-cigarette configured in this way. The cross-section is in the y-z plane and is hence orthogonal to the cross-sections in the x-y plane of FIGS. 1, 4, 5 and 10. Further, the cross-section is through the air inlet hole 214, and consequently the latching elements do not appear. The base portion 210 of the cartomizer 200 is shown received inside a recess surrounded by a peripheral upstanding portion or wall 33a of the housing 33 of the control unit 300. An outwardly facing exterior surface 210a of the base portion 210 faces an inwardly facing interior surface 33b of the wall 33a. A narrow gap exists between the two surfaces 33b and 210a.

The diametrically located pair of latching elements in this device are aligned along an axis (the x-axis) which is perpendicular to the width of the gap (along the z-axis) between the opposing surfaces 33b, 210a. Consequently, some sideways movement may arise in the y-z plane; this might be linear or angular (a rocking movement) depending on the tightness of the latching connection. To address this, one or more small protrusions 50 are provided on one or more of the opposing surfaces 33b, 201a. The protrusions 50 bridge the space between the surfaces 33b, 201a to inhibit, reduce or prevent the sideways movement, while still allowing spacing between the surfaces 33b, 201a to facilitate the connection. In this example, a pair of protrusions 50 is provided, one on each of opposite parts of the interior surface 33b of the wall 33a. The protrusions 50 have the form of bumps that extend from one surface towards the facing surface, having a domed shape in this example, but other shapes may be used. A smooth shape without corners will prevent catching of the cartomizer 200 on the control unit 300 when the two are connected or disconnected. The protrusions 50 may be formed from a hard material such as rigid plastic or from a yielding elastic material such as rubber or a similar synthetic material, and may be integrally formed with the surface that supports the protrusions 50, such as by molding, or may be separately formed and then secured to the supporting surface, by adhesive or welding for example.

Figure 12:
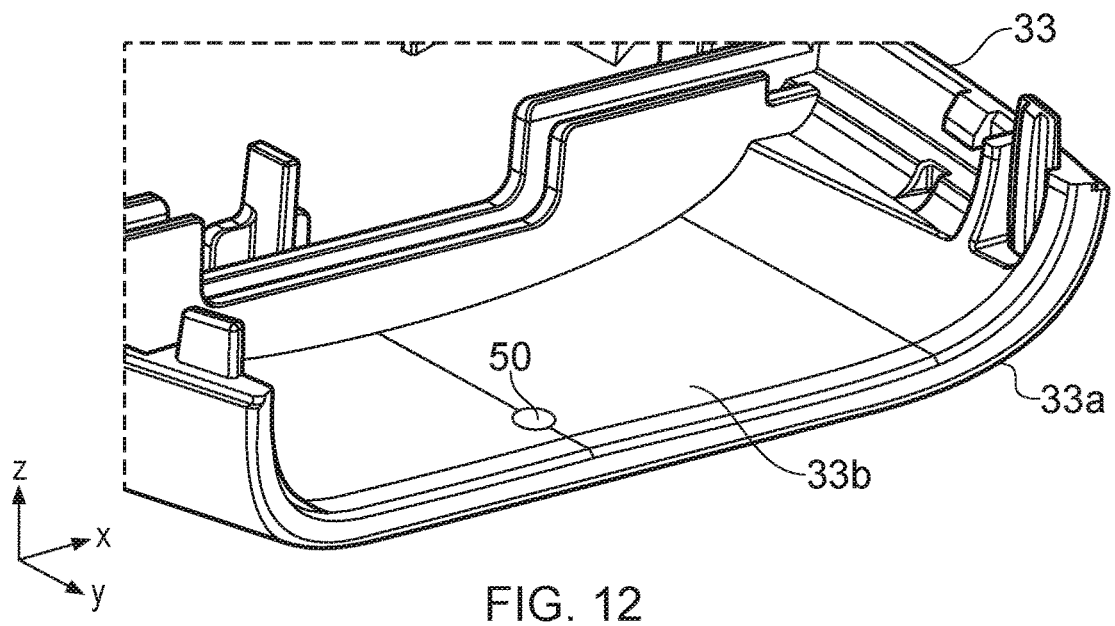
FIG. 12 shows a perspective view of part of the control unit of the example electronic cigarette of FIG. 11.

FIG. 12 shows a perspective view of the upper part of the control unit housing 33 (in this example the housing 33 is formed in two shell-like halves which are joined together in manufacture; one half only is shown). A dome-shaped bump 50 is shown protruding from the interior surface 33b of the peripheral wall 33a.

In this example, the protruding bumps 50 are located on the interior surface 33b of control unit 300 facing towards the exterior surface of the cartomizer 200, but they may instead be located on the exterior surface of the cartomizer 200 facing towards the interior surface 33b of the control unit 300. Also, protrusions 50 might be provided on the opposing surfaces of both components 200, 300. Fewer or more than two protrusions 50 might be provided. They may also be situated otherwise than as illustrated in FIG. 11. The depicted example shows protrusions 50 oppositely located along an axis roughly orthogonal to an axis along which a pair of latching elements are aligned, but protrusions may be placed on other axes, including parallel to a latching element alignment (which in the FIG. 11 example would inhibit movement along the x-axis). In general, the protrusions 50 can be provided on one or more facing surfaces of the cartomizer 200 and the control unit 300 which are non-orthogonal to the direction of the linear movement that effects the latching connection, to restrict movement in one or more directions non-parallel to the direction of linear movement, for example movement within the orthogonal plane or angular movement about axes lying in the orthogonal plane.

The example e-cigarette shown in FIG. 1 has the format of a cartomizer coupled to a control unit, where the cartomizer as a component includes both a reservoir or store for source liquid and an atomizer/vaporizer (wick or similar plus heating element). The cartomizer may be a disposable consumable item, replaceable when the reservoir is empty, for example. E-cigarettes may be configured differently, however. For example, the atomizer may be housed separately from the reservoir, and the reservoir component on its own is removable for replacement or refilling. The atomizer may then be comprised within the control unit, or may be a separate component. More generally than the cartomizer described so far, we may therefore define a component designated as a cartridge which is separably connectable to a control unit, where the cartridge includes a liquid reservoir and the control unit includes an electrical power source (battery, cell). The atomizer may be included as part of the control unit, or as part of the cartridge. In the later case, the cartridge can be considered as a cartomizer. The latching elements described herein may be used to mechanically connect a cartridge to a control unit regardless of the location of the atomizer. Hence, an e-cigarette may comprise a cartridge latched to a power unit that includes an atomizer, or a cartomizer latched to a power unit, or a cartridge latched to a power unit with an atomizer provided as a third component. Unless specifically stated and required in a particular context, all references herein to a cartomizer apply equally to a cartridge (component housing a reservoir but not an atomizer) as regards the connection of these components to a control unit by one or more latching elements. Further, the reservoir is not limited to storage of source liquid, but may instead be a store of other material or substance heatable to generate an aerosol, such as tobacco.

Note that while the latching elements are well suited for effecting a mechanical connection between separable component parts of an electronic cigarette that is not readily adapted for a connection arrangement requiring a rotatory motion (such as an e-cigarette with a non-circular transverse cross-section), the latching elements may be used to couple the cartomizer and the control unit parts of any electronic cigarette or vapor provision system in general (cylindrical or non-cylindrical), based on either liquid and non-liquid vapor sources. Embodiments of the disclosure are not limited only to the example electronic cigarettes depicted herein.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. An electronic vapor provision system comprising:
   a cartridge for storing material heatable to generate an aerosol; and
   a control unit housing a battery to provide electrical power for heating,
   wherein the cartridge and the control unit are separably connectable together by at least one latching element, the at least one latching element comprising a foot, and a leg joined at a first end to the foot by a flexible resilient joint and having a first latch member, the foot anchored within one of the cartridge or the control unit, and the at least one latching element configured such that the flexible resilient joint joins the leg and the foot in a rest position at an angle of between 70 and 110 degrees, and the other of the cartridge or the control unit having a second latch member on a surface, and positioned and configured to engage with the first latch member when the cartridge and the control unit are brought together with a substantially linear motion, and disengage with the first latch member when the cartridge and the control unit are pulled apart, the engagement and disengagement enabled by movement of the leg of the at least one latching element about the flexible resilient joint, the movement being a hinged movement that increases or decreases the angle of the flexible resilient joint from the rest position.

2. The electronic vapor provision system according to claim 1, wherein the cartridge is configured to store source liquid heatable to generate an aerosol.

3. The electronic vapor provision system according to claim 2, wherein the cartridge is a cartomizer comprising a reservoir to store the source liquid and an atomizer to generate an aerosol from the source liquid when provided with electrical power from the battery in the control unit.

4. The electronic vapor provision system according to claim 1, further comprising a resilient sealing member arranged to be compressed between the cartridge and the control unit when the cartridge and the control unit are connected together, the foot of the at least one latching element being received within the sealing member.

5. The electronic vapor provision system according to claim 4, wherein the sealing member is shaped to receive the foot.

6. The electronic vapor provision system according to claim 4, wherein compression of the sealing element when the cartridge and the control unit are connected together acts to anchor the foot and retain the at least one latching element in position.

7. The electronic vapor provision system according to claim 1, wherein the foot is anchored by being housed within shaped parts of the electronic vapor provision system.

8. The electronic vapor provision system according to claim 1, wherein the foot of the at least one latching element is anchored within the control unit and the second latch member is provided on a surface of the cartridge.

9. The electronic vapor provision system according to claim 1, wherein the first latch member comprises a protrusion from a surface of the leg of the at least one latching element and the second latch member comprises a recess formed in a surface.

10. The electronic vapor provision system according to claim 1, wherein the at least one latching element is arranged such that the movement of the leg that enables the engagement and disengagement effects an increase in the angle from the rest position, the at least one latching element assuming the rest position when the first latch member and the second latch member are engaged.

11. The electronic vapor provision system according to claim 1, wherein the at least one latching element comprises two latching elements located oppositely with respect to a central axis of the electronic vapor provision system parallel to the direction of the substantially linear motion, each latching element having a corresponding second latch member.

12. The electronic vapor provision system according to claim 1, wherein the at least one latching element is formed by die-stamping a shape cut from sheet metal.

13. The electronic vapor provision system according to claim 12, in which the sheet metal is stainless steel.

14. The electronic vapor provision system according to claim 1, wherein the electronic vapor provision system has a non-circular cross-section in a plane orthogonal to the direction of substantially linear motion where the cartridge and the control unit connect.

15. The electronic vapor provision system according to claim 1, further comprising at least one protrusion extending from a surface of the cartridge or the control unit towards a facing surface of the control unit or the cartridge when the cartridge and the control unit are connected by the at least one latching element, the surfaces being non-orthogonal to a direction of the linear motion, and the at least one protrusion inhibiting movement between the control unit and the cartridge when the control unit and the cartridge are connected by the at least one latching element.

16. A control unit for an electronic vapor provision system, the control unit separably connectable to a cartridge and housing a battery for providing electrical power to generate an aerosol from material stored in a connected cartridge, the control unit comprising:
  at least one latching element for connecting the control unit to the cartridge, the at least one latching element comprising a foot, and a leg joined at a first end to the foot by a flexible resilient joint and having a first latch member, the foot being anchored within the control unit, and the at least one latching element configured such that the flexible resilient joint joins the leg and the foot in a rest position at an angle of between 70 and 110 degrees;
  wherein the first latch member is configured to engage with a second latch member defined on a surface of the cartridge when the control unit and the cartridge are brought together with a substantially linear motion, and disengage with the second latch member when the control unit and the cartridge are pulled apart, the engagement and disengagement enabled by movement of the leg of the at least one latching element about the flexible resilient joint, the movement being a hinged movement that increases or decreases the angle of the flexible resilient joint from the rest position.

17. The control unit according to claim 16, further comprising at least one protrusion extending from a surface of the control unit towards a facing surface of the cartridge when the control unit is connected to the cartridge by the at least one latching element, the surface being non-orthogonal to a direction of the linear motion, and the at least one protrusion inhibiting movement between the control unit and the cartridge when the control unit is connected to the cartridge by the at least one latching element.

18. A cartridge for an electronic vapor provision system, the cartridge separably connectable to a control unit and configured to store material heatable to generate an aerosol when heated using electrical power from a battery housed in a connected control unit, the cartridge comprising:
  at least one latch member having the form of a protrusion or a recess defined on a surface of the cartridge, the at least one latch member configured to engage with a further latch member on a leg of a latching element anchored in the control unit when the cartridge and the control unit are brought together with a substantially linear motion, and disengage from the further latch member when the cartridge and the control unit are pulled apart, the engagement and disengagement enabled by movement of the leg of the latching element about a flexible resilient joint between the leg and a foot of the latching element by which the latching element is anchored in the control unit, the flexible resilient joint joining the leg and the foot in a rest position at an angle of between 70 and 110 degrees, and the movement being a hinged movement that increases or decreases the angle of the flexible resilient joint from the rest position.

19. The cartridge according to claim 18, wherein the cartridge is configured to store source liquid heatable to generate an aerosol.

20. The cartridge according to claim 18, wherein the cartridge is a cartomizer comprising a reservoir to store source liquid and an atomizer to generate an aerosol from the source liquid when provided with electrical power.

21. A latching element for separably connecting components of an electronic vapor provision system, and comprising:
a foot; and
a leg joined at a first end to the foot by a flexible resilient joint and having a first latch member, and the flexible resilient joint joining the leg and the foot in a rest position at an angle of between 70 and 110 degrees;
wherein the foot is configured to be anchored within a first component of the electronic vapor provision system, and the latch member is configured to engage with a further latch member defined on a surface of a second component of the electronic vapor provision system when the first component and the second component are brought together with a substantially linear motion, and disengage with the second latch member when the first component and the second component are pulled apart, the engagement and disengagement enabled by movement of the leg about the flexible resilient joint, the movement being a hinged movement that increases or decreases the angle of the flexible resilient joint from the rest position.

22. An electronic cigarette comprising:
a cartomizer housing an aerosol source; and
a control unit housing a battery,
wherein the cartomizer and the control unit are mechanically connectable together,
wherein the control unit comprises at least one latching element, the at least one latching element comprising a foot, and a leg joined to the foot by a flexible resilient joint and having a first latch member, the foot secured within the control unit, and the at least one latching element configured such that the flexible resilient joint joins the leg and the foot in a rest position at an angle of between 70 and 110 degrees, and
wherein the cartomizer has a surface shaped to define at least one second latch member positioned and configured to engage with the first latch member when the cartomizer and the control unit are brought together with a linear motion and to disengage with the first latch member when the cartomizer and the control unit are pulled apart, the engagement and disengagement enabled by movement of the leg of the at least one latching element about the flexible resilient joint, the movement being a hinged movement that increases or decreases the angle of the flexible resilient joint from the rest position.

23. An electronic cigarette comprising a cartomizer housing an aerosol source and a control unit housing a battery, wherein the cartomizer and the control unit are mechanically connectable together, and: the control unit comprises at least one latching element, the latching element comprising a foot, and a leg joined to the foot by a flexible resilient joint and having a first latch member, the foot secured within the control unit; and the cartomizer having a surface shaped to define at least one second latch member positioned and configured to engage with a first latch member when the cartomizer and the control unit are brought together with a linear motion and to disengage with the first latch member when the cartomizer and the control unit are pulled apart, the engagement and disengagement enabled by movement of the leg of the latching element about the flexible resilient joint.

* * * * *